US008846618B2

(12) United States Patent
Flink et al.

(10) Patent No.: US 8,846,618 B2
(45) Date of Patent: Sep. 30, 2014

(54) STABLE FORMULATION OF MODIFIED GLP-1

(75) Inventors: James M. Flink, Klanpenborg (DK); Silke Møller Larsen, Charlottenlund (DK); Simon Bjerregaard Jensen, Frederiksberg (DK); Dorthe Kot Engelund, Holte (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 12/785,861

(22) Filed: May 24, 2010

(65) Prior Publication Data

US 2010/0234299 A1 Sep. 16, 2010

Related U.S. Application Data

(63) Continuation of application No. 11/786,095, filed on Apr. 11, 2007, now abandoned, which is a continuation of application No. 10/185,923, filed on Jun. 27, 2002, now abandoned.

(60) Provisional application No. 60/308,325, filed on Jul. 27, 2001, provisional application No. 60/308,297, filed on Jul. 27, 2001.

(30) Foreign Application Priority Data

| Jun. 28, 2001 | (DK) | 2001 01010 |
| Jun. 28, 2001 | (DK) | 2001 01011 |
| Jul. 4, 2001 | (DK) | 2001 01052 |
| Jul. 4, 2001 | (DK) | 2001 01053 |
| Jan. 18, 2002 | (DK) | 2002 00093 |

(51) Int. Cl.
| A61K 38/26 | (2006.01) |
| A61P 3/10 | (2006.01) |
| A61P 7/12 | (2006.01) |
| C07K 14/605 | (2006.01) |

(52) U.S. Cl.
CPC ............... C07K 14/605 (2013.01); A61K 38/26 (2013.01)
USPC ............................................. 514/11.7

(58) Field of Classification Search
CPC ................. A61K 38/26; C07K 14/605
See application file for complete search history.

(56) References Cited

U.S. PATENT DOCUMENTS

| 4,468,346 A | 8/1984 | Paul et al. |
| 4,483,849 A | 11/1984 | Carter et al. |
| 5,206,219 A | 4/1993 | Desai |
| 5,272,135 A | 12/1993 | Takruri |
| 5,455,331 A | 10/1995 | Pearce |
| 5,652,216 A | 7/1997 | Kornfelt et al. |
| 5,705,483 A | 1/1998 | Galloway |
| 6,133,229 A | 10/2000 | Gibson et al. |
| 6,184,201 B1 | 2/2001 | Drucker et al. |
| 6,245,572 B1 | 6/2001 | Wall |
| 6,268,343 B1 | 7/2001 | Knudsen et al. |
| 6,274,553 B1 | 8/2001 | Furuya |
| 6,284,727 B1 | 9/2001 | Kim et al. |
| 6,380,357 B2 | 4/2002 | Hermeling et al. |
| 6,384,016 B1 * | 5/2002 | Kaarsholm ................. 514/11.7 |
| 6,440,930 B1 * | 8/2002 | Rinella, Jr. .................. 424/10.1 |
| 6,444,788 B1 | 9/2002 | Staby |
| 6,569,832 B1 | 5/2003 | Knudsen et al. |
| 6,573,237 B2 * | 6/2003 | Rinella, Jr. ..................... 514/9.9 |
| 6,586,399 B1 | 7/2003 | Drucker et al. |
| 6,844,321 B2 | 1/2005 | Arentsen |
| 7,022,674 B2 * | 4/2006 | DeFelippis et al. ............ 514/5.9 |
| 7,049,284 B2 | 5/2006 | Drucker et al. |
| 7,056,886 B2 | 6/2006 | Isaacs |
| 7,112,567 B2 | 9/2006 | Bridon et al. |
| 7,202,213 B2 | 4/2007 | Mogensen et al. |
| 7,226,990 B2 | 6/2007 | Knudsen et al. |
| 7,238,663 B2 | 7/2007 | DeFelippis et al. |
| 7,273,921 B2 | 9/2007 | Dunweber et al. |
| 7,595,293 B2 | 9/2009 | Engelund et al. |
| 7,833,531 B2 * | 11/2010 | O'Neil et al. ............... 424/178.1 |
| 8,071,103 B2 * | 12/2011 | O'Neil et al. ............... 424/178.1 |
| 8,114,833 B2 * | 2/2012 | Pedersen et al. |
| 2001/0014666 A1 | 8/2001 | Hermeling et al. |
| 2001/0027180 A1 | 10/2001 | Isaacs |
| 2002/0151467 A1 | 10/2002 | Leung |
| 2003/0060412 A1 | 3/2003 | Prouty et al. |
| 2003/0069182 A1 | 4/2003 | Rinella |
| 2003/0119734 A1 | 6/2003 | Flink et al. |
| 2003/0158101 A1 | 8/2003 | Drucker |
| 2003/0207802 A1 | 11/2003 | DeFelippis et al. |
| 2003/0220243 A1 | 11/2003 | Glaesner et al. |

(Continued)

FOREIGN PATENT DOCUMENTS

| CA | 2306024 | 4/1999 |
| CA | 2527743 | 12/2004 |

(Continued)

OTHER PUBLICATIONS

Buffers from Ruzin, 1999, Plant Microtechnique and Microscopy, accessed online on Dec. 24, 2013 at http://microscopy.berkeley.edu/Resources/instruction/buffers.html, pp. 1-6.*
D.E. Smilek et al., Proc Natl Acad Sci USA, vol. 88, pp. 9633-9637, (1991).
D. Voet and J.G. Voet, Biochem, $2^{nd}$ Ed., pp. 235-241 (1995).
H.J.C. Berendsen, Science, vol. 282, pp. 642-643 (1998).
Rudinger, In: Peptide Hormones, JA Parsons, Ed., pp. 1-7 (1976).
Sigma, http://www.sigma-genosys.com/peptide_design.asp (accessed Dec. 16, 2004).
W.S. Messer, Vasopressin and Oxytocin, http://www.neurosci.pharm.utoldeo.edu/MBC3320/vasopressin.htm, accessed online Feb. 27, 2006.

(Continued)

*Primary Examiner* — Marcela M Cordero Garcia
(74) *Attorney, Agent, or Firm* — Rosemarie R. Wilk-Orescan

(57) ABSTRACT

Pharmaceutical formulations of GLP-1 compounds and methods for preparation thereof.

14 Claims, No Drawings

(56) References Cited

U.S. PATENT DOCUMENTS

| | | |
|---|---|---|
| 2003/0220255 A1 | 11/2003 | Knudsen et al. |
| 2004/0156835 A1 | 8/2004 | Imoto et al. |
| 2004/0248782 A1 | 12/2004 | Bridon et al. |
| 2006/0084605 A1 | 4/2006 | Engelund et al. |
| 2006/0287221 A1 | 12/2006 | Knudsen et al. |
| 2009/0011976 A1 | 1/2009 | Ludvigsen et al. |

FOREIGN PATENT DOCUMENTS

| | | |
|---|---|---|
| CN | 1376166 | 10/2002 |
| EP | 0431679 | 11/1990 |
| EP | 0438767 | 12/1990 |
| EP | 699687 | 8/1995 |
| EP | 0708179 A2 | 4/1996 |
| EP | 747390 | 12/1996 |
| EP | 0923159 | 6/1999 |
| EP | 1329462 | 10/2001 |
| EP | 1424077 | 5/2002 |
| EP | 1344533 | 9/2003 |
| EP | 1396499 | 3/2004 |
| EP | 722492 | 3/2005 |
| JP | 10101696 | 4/1998 |
| JP | 2000-510813 | 8/2000 |
| JP | 2001-525371 | 12/2001 |
| JP | 2002-504908 | 2/2002 |
| JP | 2002-508332 | 3/2002 |
| JP | 2002-524514 | 8/2002 |
| JP | 2002-532557 | 10/2002 |
| JP | 2003519195 | 6/2003 |
| JP | 2004-518756 | 6/2004 |
| PA | 200101010 | 6/2001 |
| RU | 2180218 | 3/2002 |
| WO | WO9000200 | 1/1990 |
| WO | WO9219260 | 11/1992 |
| WO | 9318785 | 9/1993 |
| WO | WO9323010 | 11/1993 |
| WO | WO9522560 | 2/1995 |
| WO | 9505848 | 3/1995 |
| WO | WO95/10605 | 4/1995 |
| WO | WO9513825 | 5/1995 |
| WO | WO 96/20005 | 7/1996 |
| WO | 9624369 | 8/1996 |
| WO | WO9638469 | 12/1996 |
| WO | 98/00152 A1 | 1/1998 |
| WO | WO 98/08871 | 3/1998 |
| WO | WO9831386 | 7/1998 |
| WO | 9856406 | 12/1998 |
| WO | WO9916417 | 4/1999 |
| WO | WO99/21889 | 5/1999 |
| WO | WO 99/29336 | 6/1999 |
| WO | WO 99/30731 | 6/1999 |
| WO | WO 99/43341 | 9/1999 |
| WO | WO 99/43706 | 9/1999 |
| WO | WO 99/43707 | 9/1999 |
| WO | WO 00/15224 | 3/2000 |
| WO | WO 00/37098 | 6/2000 |
| WO | WO0037098 | 6/2000 |
| WO | WO 00/41546 | 7/2000 |
| WO | WO 00/55119 | 9/2000 |
| WO | WO 01/00223 | 1/2001 |
| WO | WO 01/43762 | 6/2001 |
| WO | 0151071 | 7/2001 |
| WO | WO 01/49314 | 7/2001 |
| WO | WO01/52937 | 7/2001 |
| WO | WO 01/55213 | 8/2001 |
| WO | WO 01/77141 | 10/2001 |
| WO | WO02067989 | 1/2002 |
| WO | 0247716 | 6/2002 |
| WO | WO 02/47715 | 6/2002 |
| WO | WO 02/48183 | 6/2002 |
| WO | 0298445 | 12/2002 |
| WO | WO 03/002136 | 1/2003 |
| WO | WO03013589 | 2/2003 |
| WO | WO 03/020201 | 3/2003 |
| WO | 03035099 | 5/2003 |
| WO | WO 03/035099 | 5/2003 |
| WO | WO 2004/029076 | 4/2004 |
| WO | WO2004105781 | 12/2004 |
| WO | WO 2005/000222 | 1/2005 |
| WO | WO2005/046716 | 5/2005 |
| WO | WO 2006/025882 | 3/2006 |

OTHER PUBLICATIONS

G.F. Stamper et al., "Accelerated Stability Testing of Proteins and Peptides: pH-Stability Profile of Insulinotropin Using Traditional Arrheneius and Non-Linear Fitting Analysis", Drug Development and Industrial Pharmacy, 1995, vol. 21, No. 13, pp. 1503-1511.

H. Qi et al., "Stability and Stabilization of Insulinotropin in a Dextran Formulation", PDA Journal of Pharmaceutical Science & Technology, vol. 49, No. 6, Nov.-Dec. 1995, pp. 289-293.

European Pharmacopoeia, 2007, vol. 1, p. 730, Council of Europe-Strasbourg.

Non-Final Office Action mailed Dec. 9, 2009 in U.S. Appl. No. 12/184,531 filed Aug. 1, 2008 by Juul-Mortensen.

Bailey et al. The Kinetics of Enzyme-Catalysed Reactions Biochemical Engineering Fundamentals, 2nd Ed., pp. 129-148 (1986).

Blundell, T.L., Lefébvre P.J. (Ed), 1983, Vol. 66, p. 37-55.

S.E. Bondos & A. Bicknell, Detection and Prevention of Protein Aggregation Before During and After Purification, Analytical Biochemistry, 2003, 223-231, vol. 316, Academic Press.

Council of Europe—Strasbourg, European Pharmacopoeia, 2007, vol. 1, p. 730.

Entry for Glycerin in Drugs.Com (www.drugs.com/ppa/glycerin-glycerol.Html), Printed Aug. 4, 2009.

Malendowicz, L.K. et al., "Preproglucagon Derived Peptides and Thyrotropin (TSH) Secretion in the Rat: Robust and Sustained Lowering of Blood TSH Levels in Extendin-4 Injected Animals", International Journal of Molecular Medicine, vol. 10, p. 327-331 (2002).

Senderoff, R.I. et al, Consideration of Conformational Transitions and Racemization During Process Development of Recombinant Glucagon-Like Peptide-1, Journal of Pharmaceutical Sciences, 1998, 183-189, vol. 87—No. 2, American Chemical Society & American Pharm. Assc.

Tsoka et al, Selective Flocculation Ands Precipitation for the Improvement of Virus-Like Particle Recovery From Yeast Homogenate, Biotechnol Prog. vol. 16(4), pp. 661-667 (2000).

Shinotesuto, Patentabstracts of Japan for JP10101696.

Brittain, Harry G., Buffers, Buffering Agents, and Ionic Equilibria, Encyclopedia of Pharmaceutical Technology, p. 385, 2007.

Non-Final Office Action in U.S. Appl. No. 11/290,634, filed Nov. 30, 2005, Inventors: Juul-Mortensen et al. Sent Jun. 30, 2008.

Non-Final Office Action in U.S. Appl. No. 11/290,634, filed Nov. 30, 2005, Inventors: Juul-Mortensen et al. Sent Nov. 9, 2007.

Non-Final Office Action in U.S. Appl. No. 11/290,635, filed Nov. 30, 2005 , Inventors: Juul-Mortensen et al. Sent Feb. 2, 2007.

Non-Final Office Action in U.S. Appl. No. 11/290,635, filed Nov. 30, 2005, Inventors: Juul-Mortensen et al. Sent Feb. 2, 2007.

Non-Final Office Action in U.S. Appl. No. 11/365,274, filed Mar. 1, 2006, Inventors: Schlein et al. Sent Aug. 20, 2007.

Non-Final Office Action in U.S. Appl. No. 11/365,274, filed Mar. 1, 2006, Inventors: Schlein et al. Sent Feb. 5, 2007.

Non-Final Office Action in U.S. Appl. No. 11/365,274, filed Mar. 1, 2006, Inventors: Schlein et al. Sent Jan. 28, 2009.

Non-Final Office Action in U.S. Appl. No. 11/435,977, filed May 17, 2006, Inventors: Pedersen et al. Sent Dec. 2, 2008.

Non-Final Office Action in U.S. Appl. No. 10/185,923, filed Jun. 27, 2002, Inventors: Flink et al. Sent Mar. 10, 2006.

Non-Final Office Action in U.S. Appl. No. 10/185,923, filed June 27, 2002, Inventors: Flink et al. Sent Mar. 10, 2006.

Non-Final Office Action in U.S. Appl. No. 11/786,095, filed Apr. 11,2007, Inventors: Flink et al. Sent Feb. 24, 2009.

Non-Final Office Action in U.S. Appl. No. 12/343,722, filed Dec. 24, 2008, Inventors: Flink et al. Sent May 22, 2009.

Final Office Action in U.S. Appl. No. 11/290,635, filed Nov. 30, 2005, Inventors: Juul-Mortensen et al. Sent Sep. 5, 2007.

Final Office Action in U.S. Appl. No. 11/365,274, filed Mar. 1, 2006, Inventors: Schlein et al. Sent Apr. 4, 2008.

(56) References Cited

OTHER PUBLICATIONS

Final Office Action in U.S. Appl. No. 11/365,274, filed Mar. 1, 2006, Inventors: Schlein et al. Sent Aug. 12, 2009.
Final Office Action in U.S. Appl. No. 11/435,977, filed May 17, 2006, Inventors: Pedersen et al. Sent Jun. 25, 2009.
Final Office Action in U.S. Appl. No. 10/185,923, filed Jun. 27, 2002, Inventors: Flink et al. Sent Dec. 12, 2006.
Final Office Action in U.S. Appl. No. 10/185,923, filed Jun. 27, 2002, Inventors: Flink et al. Sent June 14, 2005.
Final Office Action in U.S. Appl. No. 10/185,923, filed Jun. 27, 2002, Inventors: Flink et al. Sent June 30, 2008.
Final Office Action in U.S. Appl. No. 11/786,095, filed Apr. 11,2007, Inventors: Flink et al. Sent Nov. 24, 2009.
Eli Lilly & Co., Humalog Lispro Injection, USP Product Information.
European Pharmacopoeia, 3RD Edition, 2.2.3, 1997, pp. 17-8, Council of Europe-Strasbourg.
Frokjaer & Hovgaard, Pharmaceutical Formulation Development of, 2000, pp. 145-148 & 150-151.
Further Experimental Data Dated Jun. 22, 2009.
Gonzales, Johnny C., Declaration of (Including Curriculum Vita) Dated Nov. 1, 2010.
Knudsen, L.B. et al., Potent Derivatives of Glucogon-Like Peptide-1, Journal of Medicinal Chemistry, 2000, vol. 43, pp. 1664-1669.
Kristensen, H.G., Almen Farmaci, 2000, pp. 273-274, 281.
Lund, Walter, Editor, The Pharmaceutical Codex, 12th Edition, 1994, The Pharmaceutical Press, London, pp. 98-99.
Mack Publishing Co., Remington's Pharmaceutical Sciences, 16th Edition,1980, Pt. 79, p. 1406.
Mack Publishing Co., Remington's Pharmaceutical Sciences, 18th Edition, 1990, Chapter 84, pp. 1545-1550.
Martin A. et al., Physical Pharmacy; Physical Chemical Principles in the Pharmaceutical Sciences, 1983, 3rd Edition, pp. 222-225.
Sigma Product Information on Gly-Gly Buffer Dated Mar. 16, 2010.
United States Pharmacopoeia, 24th Edition, 1999, pp. 1977-1978.
Villaneuva_Penacarril, M.L., Potent Glycognic Effect of GLP-1(7-36) Amide in Rat Skeletal Muscle, Diabetologia, 1994, vol. 37, pp. 1163-1166.
Wang & Hansen, Journal of Parenteral Science & Technology, 1988, vol. 42, pp. 4-26.
Wang et. al., Aggregation of Therapeutic Proteins, 2010, p. 241.
Weinstein, Sharon, Plumer's Principles & Practice of Intravenous, 2006, vol. 8 (8), pp. 124-128.
Duma et al., Pharmaceutical Dosage Forms: Parenteral Medications, vol. 1, 2nd Edition, p. 20.
Stenesh, J., Foundation of Biochemistry II Biomolecules, 1998, pp. 67-69.
Chou, J. Z. et al., Journal of Pharmaceutical Sciences, a Radioimmunoassay for LY315902, an Analog of Glucagon-Like Insulinotropic Pepride, and Its Application in the Study of Canine Pharmacokinetics, vol. 86(7), pp. 768-773 (1997).
http://www.copewithcytokines.de/cope.cgi?key=insulinotropin; (Host Ibelgauft's COPE: Cytokines & Cells Online pathfinder Encyclopedia; insulinotropin), 1987.
http://www.copewithcytokineslde/cope.cgi?key=GLP%2dl; (Host Ibelgauft's COPE: Cytokines & Cells Online Pathfinder Encyclopedia; GLP-1), 1987.
http://www.fermantas.com/techinfo/appendix/appendixtables1.htm, 'Temperature Dependence of the Ph for Commonly Used Buffers' + 'Temperature Dependence of the Ph of 50 mm Tris-HCL Solutions', 1966.
Larsen, P.J. et al., Systemic Administration of the Logn Acting GLP-1, Diabetes, 2000 vol. 50, pp. 2530-2539.
N. Good et al., "Hydrogen Ion Buffers for Biological Research", Biochemistry, 1966, vol. 5, No. 2, pp. 467-477.
http://www.sigmaaldrich.com/life-science/metabolomics/enzyme-explorer/learning-center/assay-library/assays-by-enzyme-name-ii.html#%20G%, Enzymatic Assay of Glucose-6-Phosphate obtained from the Sigma Aldrich website, 1996.
Singh, S. et al. AAPS Pharmscitech, vol. 4(3), pp. 334-342 (2003).
Skovgaard et al., "Using Evolutionary Information and Ancestral Sequences to Understand the Sequence-Function Relationship in GLP-1 Agonists," J. Mol. Bio., 2006, vol. 363, pp. 977-988.
Pridal et al., "Absorption of Glucagon-Like Peptide-1 Can Be Protracted by Zinc or Protamine", International Journal of Pharmaceutics, 1996, vol. 136, pp. 53-59.

\* cited by examiner

STABLE FORMULATION OF MODIFIED GLP-1

CROSS-REFERENCE TO RELATED APPLICATIONS

This application is a continuation of U.S. application Ser. No. 11/786,095 filed on Apr. 11, 2007, which is a continuation of U.S. application Ser. No. 10/185,923 filed on Jun. 27, 2002 and claims priority under 35 U.S.C. 119 of Danish Application No. PA 2001 01010 filed Jun. 28, 2001; Danish Application No. PA 2001 01011 filed Jun. 28, 2001; Danish Application No. PA 2001 01052 filed Jul. 4, 2001; Danish Application No. PA 2001 01053 filed Jul. 4, 2001; and Danish Application No. PA 2002 00093 filed Jan. 18, 2002; and U.S. Provisional Applications No. 60/308,325 filed Jul. 27, 2001 and 60/308,297 filed Jul. 27, 2001, the contents of which are fully incorporated herein by reference.

FIELD OF THE INVENTION

The present invention relates to pharmaceutical formulations comprising GLP-1 compounds, uses thereof and methods for preparing said formulations.

BACKGROUND OF THE INVENTION

Peptides are widely used in medical practice, and since they can be produced by recombinant DNA technology it can be expected that their importance will increase also in the years to come.

The hormones regulating insulin secretion belong to the so-called enteroinsular axis, designating a group of hormones, released from the gastrointestinal mucosa in response to the presence and absorption of nutrients in the gut, which promote an early and potentiated release of insulin. The enhancing effect on insulin secretion, the so-called incretin effect, is probably essential for a normal glucose tolerance. Many of the gastrointestinal hormones, including gastrin and secretin (cholecystokinin is not insulinotropic in man), are insulinotropic, but the only physiologically important ones, those that are responsible for the incretin effect, are the glucose-dependent insulinotropic polypeptide, GIP, and glucagon-like peptide-1 (GLP-1). Because of its insulinotropic effect, GIP, isolated in 1973 immediately attracted considerable interest among diabetologists. However, numerous investigations carried out during the following years clearly indicated that a defective secretion of GIP was not involved in the pathogenesis of insulin dependent diabetes mellitus (IDDM) or non insulin-dependent diabetes mellitus (NIDDM). Furthermore, as an insulinotropic hormone, GIP was found to be almost ineffective in NIDDM. The other incretin hormone, GLP-1 is the most potent insulinotropic substance known. Unlike GIP, it is surprisingly effective in stimulating insulin secretion in NIDDM patients. In addition, and in contrast to the other insulinotropic hormones (perhaps with the exception of secretin) it also potently inhibits glucagon secretion. Because of these actions it has pronounced blood glucose lowering effects particularly in patients with NIDDM.

GLP-1, a product of the proglucagon, is one of the youngest members of the secretin-VIP family of peptides, but is already established as an important gut hormone with regulatory function in glucose metabolism and gastrointestinal secretion and metabolism. The glucagon gene is processed differently in the pancreas and in the intestine. In the pancreas, the processing leads to the formation and parallel secretion of 1) glucagon itself, occupying positions 33-61 of proglucagon (PG); 2) an N-terminal peptide of 30 amino acids (PG (1-30)) often called glicentin-related pancreatic peptide, GRPP; 3) a hexapeptide corresponding to PG (64-69); 4) and, finally, the so-called major proglucagon fragment (PG (72-158)), in which the two glucagon-like sequences are buried. Glucagon seems to be the only biologically active product. In contrast, in the intestinal mucosa, it is glucagon that is buried in a larger molecule, while the two glucagon-like peptides are formed separately.

While much attention has been focused on the pharmacological properties of acylated GLP-1 compounds, hitherto little is known about their physico-chemical and solution structural properties. Such knowledge is a prerequisite for rational handling during e.g. production, purification and formulation work and is eventually important for understanding of the structural basis for the protraction mechanism.

It is an important technical challenge to ensure prolonged stability during storage (shelf life) of many protein based drug products due to the inherent lability of macromolecules. Hence, proteins are sensitive to both chemical and physical degradation unlike many small molecules. Chemical degradation involves covalent bonds, such as hydrolysis, racemization, oxidation or crosslinking. Physical degradation involves conformational changes relative to the native structure, which includes loss of higher order structure, aggregation, precipitation or adsorption to surfaces. GLP-1 is known to be prone to instability due to aggregation. Both degradation pathways may ultimately lead to loss of biological activity of the protein drug.

GLP-1 and analogues of GLP-1 and fragments thereof are potentially useful i.a. in the treatment of type 1 and type 2 diabetes. However, solubility limitations and the low stability against the actions of endogenous diaminopeptidyl peptidase limits the usefulness of these compounds, and thus there still is a need for improvements in this field.

In WO 99/43341 are disclosed certain pharmaceutical formulations comprising GLP-1 having a lipophilic substituent. All of the disclosed formulations are maintained at pH 7.4.

In WO 00/37098 are disclosed shelf-stable formulations comprising GLP-1, a preservative, and a tonicity modifier, at pH 8.2 to 8.8.

Human GLP-1 is a 37 amino acid residue peptide originating from preproglucagon which is synthesised i.a. in the L-cells in the distal ileum, in the pancreas and in the brain. Processing of preproglucagon to give GLP-1(7-36)amide, GLP-1(7-37) and GLP-2 occurs mainly in the L-cells. A simple system is used to describe fragments and analogues of this peptide. Thus, for example, Val$^8$-GLP-1(7-37) (or Val8GLP-1(7-37)) designates a fragment of GLP-1 formally derived from GLP-1 by deleting the amino acid residues Nos. 1 to 6 and substituting the naturally occurring amino acid residue in position 8 (Ala) by Val. Similarly, Lys$^{34}$(N$^\epsilon$-tetradecanoyl)-GLP-1(7-37) designates GLP-1(7-37) wherein the ε-amino group of the Lys residue in position 34 has been tetradecanoylated. For convenience the amino acid sequence of GLP-1 (7-37) is given below, wherein the N-terminal His is no. 7 and the C-terminal Gly is no. 37:

(SEQ ID NO.: 1)
His-Ala-Glu-Gly-Thr-Phe-Thr-Ser-Asp-Val-Ser-

Ser-Tyr-Leu-Glu-Gly-Gln-Ala-Ala-Lys-Glu-Phe-

Ile-Ala-Trp-Leu-Val-Lys-Gly-Arg-Gly.

Where reference in this text is made to C-terminally extended GLP-1 analogues, the amino acid residue in position 38 is Arg unless otherwise indicated, the optional amino acid residue in position 39 is also Arg unless otherwise indicated and the optional amino acid residue in position 40 is Asp unless otherwise indicated. Also, if a C-terminally extended analogue extends to position 41, 42, 43, 44 or 45, the amino acid sequence of this extension is as in the corresponding sequence in human preproglucagon unless otherwise indicated.

SUMMARY OF THE INVENTION

We have discovered that certain modified GLP-1 or analogues thereof when formulated in aqueous solution together with a buffer, are physically stable at high concentrations of the modified GLP-1 or analogues thereof, when kept in the pH range from about 7 to about 10. The present formulations are physically stable within a given shelf life period at the recommended storage temperature (typically 2-3 years at 2-8° C.). Furthermore, the present formulations are physically stable during in-use (typically 1 month at accelerated temperatures e.g. 25° C. or 37° C.). The formulations of the invention are also chemically stable thus rendering them shelf-stable and suitable for invasive (eg. injection, subcutaneous injection, intramuscular, intravenous or infusion) as well as non-invasive (eg nasal or pulmonary, transdermal or transmucosal e.g. buccal) means of administration. When the inventive formulation comprising a GLP-1 compound was compared to the same formulation comprising GLP-1(7-37) substituted for the GLP-1 compound, the physical stability was increased considerably, and typically the shelf-life was increased from a few seconds to several months in the tests used.

One object of the present invention is to provide a pharmaceutical formulation comprising a GLP-1 compound, and a buffer, wherein said GLP-1 compound is GLP-1(7-37) or an analogue thereof wherein an amino acid residue of the parent peptide has a lipophilic substituent attached optionally via a spacer, wherein said GLP-1 compound is present in a concentration from 0.1 mg/ml to 100 mg/ml, and wherein said formulation has a pH from 7.0 to 10;

Another object of the present invention is to provide a method of preparing a physically stable pharmaceutical formulation of a GLP-1 compound wherein said GLP-1 compound is GLP-1(7-37) or an analogue thereof wherein an amino acid residue of the parent peptide has a lipophilic substituent attached optionally via a spacer, comprising preparing a formulation containing the GLP-1 compound, and a buffer, wherein said GLP-1 compound is present in a concentration from 0.1 mg/ml to 100 mg/ml, and wherein said formulation has a pH from 7.0 to 10.

In one aspect of the invention the formulation contains a GLP-1 compound in a concentration from 1 mg/ml to 100 mg/ml.

In another aspect of the invention the formulation has a pH from 7.5 to 10.

In one embodiment the GLP-1 compound is $Arg^{34}$, $Lys^{26}$ (N-ε-(γ-Glu(N-α-hexadecanoyl)))-GLP-1(7-37).

DESCRIPTION OF THE INVENTION

In one aspect the invention relates to a pharmaceutical formulation comprising a GLP-1 compound, and a buffer, wherein said GLP-1 compound is GLP-1(7-37) or an analogue thereof wherein an amino acid residue of the parent peptide has a lipophilic substituent attached optionally via a spacer, wherein said GLP-1 compound is present in a concentration from 0.1 mg/ml to 100 mg/ml, and wherein said formulation has a pH from 7.0 to 10;
provided that if an isotonic agent is present and pH is 7.4 then mannitol or NaCl is not the isotonic agent.

In another aspect the invention relates to a pharmaceutical formulation comprising a GLP-1 compound, and a buffer, wherein said GLP-1 compound is GLP-1(7-37) or an analogue thereof wherein an amino acid residue of the parent peptide has a lipophilic substituent attached optionally via a spacer, wherein said GLP-1 compound is present in a concentration from 1 mg/ml to 100 mg/ml, and wherein said formulation has a pH from 7.0 to 10;
provided that if an isotonic agent is present and pH is 7.4 then mannitol or NaCl is not the isotonic agent.

In a further aspect the invention relates to a pharmaceutical formulation comprising a GLP-1 compound, and a buffer, wherein said GLP-1 compound is GLP-1(7-37) or an analogue thereof wherein an amino acid residue of the parent peptide has a lipophilic substituent attached optionally via a spacer, wherein said GLP-1 compound is present in a concentration from 0.1 mg/ml or above, and wherein said formulation has a pH from 7.0 to 10.

In a further aspect the invention relates to a pharmaceutical formulation comprising a GLP-1 compound, and a buffer, wherein said GLP-1 compound is GLP-1(7-37) or an analogue thereof wherein an amino acid residue of the parent peptide has a lipophilic substituent attached optionally via a spacer, wherein said GLP-1 compound is present in a concentration from 1 mg/ml or above, and wherein said formulation has a pH from 7.0 to 10.

In a further aspect the invention relates to a pharmaceutical formulation comprising a GLP-1 compound, and a buffer, wherein said GLP-1 compound is GLP-1(7-37) or an analogue thereof, wherein an amino acid residue of the parent peptide has a lipophilic substituent attached optionally via a spacer, wherein said GLP-1 compound is present in a concentration from 0.1 mg/ml to 100 mg/ml, and wherein said formulation has a pH from 7.0 to 10.

In a further aspect the invention relates to a pharmaceutical formulation comprising a GLP-1 compound, and a buffer, wherein said GLP-1 compound is GLP-1(7-37) or an analogue thereof, wherein an amino acid residue of the parent peptide has a lipophilic substituent attached optionally via a spacer, wherein said GLP-1 compound is present in a concentration from 1 mg/ml to 100 mg/ml, and wherein said formulation has a pH from 7.0 to 10.

In a further aspect the invention relates to a method of preparing a physically stable pharmaceutical formulation of a GLP-1 compound wherein said GLP-1 compound is GLP-1(7-37) or an analogue thereof, wherein an amino acid residue of the parent peptide has a lipophilic substituent attached optionally via a spacer, comprising preparing a formulation containing the GLP-1 compound, and a buffer, wherein said GLP-1 compound is present in a concentration from 0.1 mg/ml or above, and wherein said formulation has a pH from 7.0 to 10.

In a further aspect the invention relates to a method of preparing a physically stable pharmaceutical formulation of a GLP-1 compound wherein said GLP-1 compound is GLP-1(7-37) or an analogue thereof, wherein an amino acid residue of the parent peptide has a lipophilic substituent attached optionally via a spacer, comprising preparing a formulation containing the GLP-1 compound, and a buffer, wherein said GLP-1 compound is present in a concentration from 1 mg/ml or above, and wherein said formulation has a pH from 7.0 to 10.

In a further aspect the invention relates to a method of preparing a physically stable pharmaceutical formulation of a GLP-1 compound wherein said GLP-1 compound is GLP-1 (7-37) or an analogue thereof, wherein an amino acid residue of the parent peptide has a lipophilic substituent attached optionally via a spacer, comprising preparing a formulation containing the GLP-1 compound, and a buffer, wherein said GLP-1 compound is present in a concentration from 0.1 mg/ml to 100 mg/ml, and wherein said formulation has a pH from 7.0 to 10.

In a further aspect the invention relates to a method of preparing a physically stable pharmaceutical formulation of a GLP-1 compound wherein said GLP-1 compound is GLP-1 (7-37) or an analogue thereof, wherein an amino acid residue of the parent peptide has a lipophilic substituent attached optionally via a spacer, comprising preparing a formulation containing the GLP-1 compound, and a buffer, wherein said GLP-1 compound is present in a concentration from 1 mg/ml to 100 mg/ml, and wherein said formulation has a pH from 7.0 to 10.

In a further aspect the invention relates to a method of preparing a physically stable pharmaceutical formulation of a GLP-1 compound wherein said GLP-1 compound is GLP-1 (7-37) or an analogue thereof, wherein an amino acid residue of the parent peptide has a lipophilic substituent attached optionally via a spacer, comprising preparing a formulation containing the GLP-1 compound, water, and a buffer, wherein said GLP-1 compound is present in a concentration from 0.1 mg/ml to 100 mg/ml, and wherein said formulation has a pH from 7.0 to 10.

In a further aspect the invention relates to a method of preparing a physically stable pharmaceutical formulation of a GLP-1 compound wherein said GLP-1 compound is GLP-1 (7-37) or an analogue thereof, wherein an amino acid residue of the parent peptide has a lipophilic substituent attached optionally via a spacer, comprising preparing a formulation containing the GLP-1 compound, water, and a buffer, wherein said GLP-1 compound is present in a concentration from 1 mg/ml to 100 mg/ml, and wherein said formulation has a pH from 7.0 to 10.

In a further aspect the invention relates to a method of preparing a physically stable pharmaceutical formulation of a GLP-1 compound wherein said GLP-1 compound is GLP-1 (7-37) or an analogue thereof, wherein an amino acid residue of the parent peptide has a lipophilic substituent attached optionally via a spacer, comprising preparing an aqueous solution containing the GLP-1 compound, and a buffer, wherein said GLP-1 compound is present in a concentration from 0.1 mg/ml to 100 mg/ml, and wherein said formulation has a pH from 7.0 to 10.

In a further aspect the invention relates to a method of preparing a physically stable pharmaceutical formulation of a GLP-1 compound wherein said GLP-1 compound is GLP-1 (7-37) or an analogue thereof, wherein an amino acid residue of the parent peptide has a lipophilic substituent attached optionally via a spacer, comprising preparing an aqueous solution containing the GLP-1 compound, and a buffer, wherein said GLP-1 compound is present in a concentration from 1 mg/ml to 100 mg/ml, and wherein said formulation has a pH from 7.0 to 10.

In a further aspect the invention relates to a method of preparing a physically stable pharmaceutical formulation of a GLP-1 compound wherein said GLP-1 compound is GLP-1 (7-37) or an analogue thereof, wherein an amino acid residue of the parent peptide has a lipophilic substituent attached optionally via a spacer, comprising preparing a formulation containing the GLP-1 compound, water, and a buffer, wherein said GLP-1 compound is present in a concentration from 0.1 mg/ml to 100 mg/ml, and wherein said formulation has a pH from 7.5 to 10.

In a further aspect the invention relates to a method of preparing a physically stable pharmaceutical formulation of a GLP-1 compound wherein said GLP-1 compound is GLP-1 (7-37) or an analogue thereof, wherein an amino acid residue of the parent peptide has a lipophilic substituent attached optionally via a spacer, comprising preparing a formulation containing the GLP-1 compound, water, and a buffer, wherein said GLP-1 compound is present in a concentration from 1 mg/ml to 100 mg/ml, and wherein said formulation has a pH from 7.5 to 10.

In a further aspect the invention relates to a method of preparing a physically stable pharmaceutical formulation of a GLP-1 compound wherein said GLP-1 compound is GLP-1 (7-37) or an analogue thereof, wherein an amino acid residue of the parent peptide has a lipophilic substituent attached optionally via a spacer, comprising preparing an aqueous solution containing the GLP-1 compound, and a buffer, wherein said GLP-1 compound is present in a concentration from 0.1 mg/ml to 100 mg/ml, and wherein said formulation has a pH from 7.5 to 10.

In a further aspect the invention relates to a method of preparing a physically stable pharmaceutical formulation of a GLP-1 compound wherein said GLP-1 compound is GLP-1 (7-37) or an analogue thereof, wherein an amino acid residue of the parent peptide has a lipophilic substituent attached optionally via a spacer, comprising preparing an aqueous solution containing the GLP-1 compound, and a buffer, wherein said GLP-1 compound is present in a concentration from 1 mg/ml to 100 mg/ml, and wherein said formulation has a pH from 7.5 to 10.

In a further aspect the invention relates to a method of preparing a physically stable pharmaceutical formulation of a GLP-1 compound wherein said GLP-1 compound is GLP-1 (7-37) or an analogue thereof, wherein an amino acid residue of the parent peptide has a lipophilic substituent attached optionally via a spacer, comprising preparing a formulation containing the GLP-1 compound, and a buffer, wherein said GLP-1 compound is present in a concentration from 0.1 mg/ml to 100 mg/ml, and wherein said formulation has a pH from 7.0 to 10; provided that if an isotonic agent is present and pH is 7.4 then mannitol or NaCl is not the isotonic agent.

In a further aspect the invention relates to a method of preparing a physically stable pharmaceutical formulation of a GLP-1 compound wherein said GLP-1 compound is GLP-1 (7-37) or an analogue thereof, wherein an amino acid residue of the parent peptide has a lipophilic substituent attached optionally via a spacer, comprising preparing a formulation containing the GLP-1 compound, and a buffer, wherein said GLP-1 compound is present in a concentration from 1 mg/ml to 100 mg/ml, and wherein said formulation has a pH from 7.0 to 10; provided that if an isotonic agent is present and pH is 7.4 then mannitol or NaCl is not the isotonic agent.

In one embodiment of the invention the pharmaceutical formulation is an aqueous formulation, i.e. a formulation comprising water. Such formulation is typically a solution or a suspension. In a further embodiment of the invention the pharmaceutical formulation is an aqueous solution. The term "aqueous formulation" is defined as a formulation comprising at least 50% w/w water. Likewise, the term "aqueous solution" is defined as a solution comprising at least 50% w/w water, and the term "aqueous suspension" is defined as a suspension comprising at least 50% w/w water.

In another embodiment the pharmaceutical formulation is a freeze-dried formulation, whereto the physician or the patient adds the solvent prior to use.

In a further aspect the invention relates to a pharmaceutical formulation comprising an aqueous solution of a GLP-1 compound, and a buffer, wherein said GLP-1 compound is GLP-1(7-37) or an analogue thereof wherein an amino acid residue of the parent peptide has a lipophilic substituent attached optionally via a spacer, wherein said GLP-1 compound is present in a concentration from 0.1 mg/ml or above, and wherein said formulation has a pH from 7.0 to 10.

In a further aspect the invention relates to a pharmaceutical formulation comprising an aqueous solution of a GLP-1 compound, and a buffer, wherein said GLP-1 compound is GLP-1(7-37) or an analogue thereof wherein an amino acid residue of the parent peptide has a lipophilic substituent attached optionally via a spacer, wherein said GLP-1 compound is present in a concentration from 1 mg/ml or above, and wherein said formulation has a pH from 7.0 to 10.

In a further aspect the invention relates to a pharmaceutical formulation comprising an aqueous solution of a GLP-1 compound, and a buffer, wherein said GLP-1 compound is GLP-1(7-37) or an analogue thereof, wherein an amino acid residue of the parent peptide has a lipophilic substituent attached optionally via a spacer, wherein said GLP-1 compound is present in a concentration from 0.1 mg/ml to 100 mg/ml, and wherein said formulation has a pH from 7.0 to 10.

In a further aspect the invention relates to a pharmaceutical formulation comprising an aqueous solution of a GLP-1 compound, and a buffer, wherein said GLP-1 compound is GLP-1(7-37) or an analogue thereof, wherein an amino acid residue of the parent peptide has a lipophilic substituent attached optionally via a spacer, wherein said GLP-1 compound is present in a concentration from 1 mg/ml to 100 mg/ml, and wherein said formulation has a pH from 7.0 to 10.

In a further aspect the invention relates to a pharmaceutical formulation comprising an aqueous solution of a GLP-1 compound, and a buffer, wherein said GLP-1 compound is GLP-1(7-37) or an analogue thereof, wherein an amino acid residue of the parent peptide has a lipophilic substituent attached optionally via a spacer, wherein said GLP-1 compound is present in a concentration from 0.1 mg/ml to 100 mg/ml, and wherein said formulation has a pH from 7.0 to 10; provided that if an isotonic agent is present and pH is 7.4 then mannitol or NaCl is not the isotonic agent.

In a further aspect the invention relates to a pharmaceutical formulation comprising an aqueous solution of a GLP-1 compound, and a buffer, wherein said GLP-1 compound is GLP-1(7-37) or an analogue thereof, wherein an amino acid residue of the parent peptide has a lipophilic substituent attached optionally via a spacer, wherein said GLP-1 compound is present in a concentration from 1 mg/ml to 100 mg/ml, and wherein said formulation has a pH from 7.0 to 10; provided that if an isotonic agent is present and pH is 7.4 then mannitol or NaCl is not the isotonic agent.

In a further aspect the invention relates to a method of preparing a physically stable pharmaceutical formulation of a GLP-1 compound wherein said GLP-1 compound is GLP-1(7-37) or an analogue thereof, wherein an amino acid residue of the parent peptide has a lipophilic substituent attached optionally via a spacer, comprising preparation of an aqueous solution containing the GLP-1 compound, and a buffer, wherein said GLP-1 compound is present in a concentration from 0.1 mg/ml or above, and wherein said formulation has a pH from 7.0 to 10.

In a further aspect the invention relates to a method of preparing a physically stable pharmaceutical formulation of a GLP-1 compound wherein said GLP-1 compound is GLP-1(7-37) or an analogue thereof, wherein an amino acid residue of the parent peptide has a lipophilic substituent attached optionally via a spacer, comprising preparation of an aqueous solution containing the GLP-1 compound, and a buffer, wherein said GLP-1 compound is present in a concentration from 1 mg/ml or above, and wherein said formulation has a pH from 7.0 to 10.

In a further aspect the invention relates to a method of preparing a physically stable pharmaceutical formulation of a GLP-1 compound wherein said GLP-1 compound is GLP-1(7-37) or an analogue thereof, wherein an amino acid residue of the parent peptide has a lipophilic substituent attached optionally via a spacer, comprising preparation of an aqueous solution containing the GLP-1 compound, and a buffer, wherein said GLP-1 compound is present in a concentration from 0.1 mg/ml to 100 mg/ml, and wherein said formulation has a pH from 7.0 to 10.

In a further aspect the invention relates to a method of preparing a physically stable pharmaceutical formulation of a GLP-1 compound wherein said GLP-1 compound is GLP-1(7-37) or an analogue thereof, wherein an amino acid residue of the parent peptide has a lipophilic substituent attached optionally via a spacer, comprising preparation of an aqueous solution containing the GLP-1 compound, and a buffer, wherein said GLP-1 compound is present in a concentration from 1 mg/ml to 100 mg/ml, and wherein said formulation has a pH from 7.0 to 10.

In a further aspect the invention relates to a method of preparing a physically stable pharmaceutical formulation of a GLP-1 compound wherein said GLP-1 compound is GLP-1(7-37) or an analogue thereof, wherein an amino acid residue of the parent peptide has a lipophilic substituent attached optionally via a spacer, comprising preparation of an aqueous solution containing the GLP-1 compound, and a buffer, wherein said GLP-1 compound is present in a concentration from 0.1 mg/ml to 100 mg/ml, and wherein said formulation has a pH from 7.0 to 10; provided that if an isotonic agent is present and pH is 7.4 then mannitol or NaCl is not the isotonic agent.

In a further aspect the invention relates to a method of preparing a physically stable pharmaceutical formulation of a GLP-1 compound wherein said GLP-1 compound is GLP-1(7-37) or an analogue thereof, wherein an amino acid residue of the parent peptide has a lipophilic substituent attached optionally via a spacer, comprising preparation of an aqueous solution containing the GLP-1 compound, and a buffer, wherein said GLP-1 compound is present in a concentration from 1 mg/ml to 100 mg/ml, and wherein said formulation has a pH from 7.0 to 10; provided that if an isotonic agent is present and pH is 7.4 then mannitol or NaCl is not the isotonic agent.

In a further aspect the present invention relates to a method of reducing blood glucose levels, treating diabetes type I, diabetes type II, obesity, or inhibiting gastric acid secretion, inhibiting apoptosis of β-cells, or stimulating the proliferation of 3-cells, comprising administering to a patient in need thereof an effective amount of a pharmaceutical formulation comprising an aqueous solution of a GLP-1 compound, and a buffer, wherein said GLP-1 compound is GLP-1(7-37) or an analogue thereof wherein an amino acid residue of the parent peptide has a lipophilic substituent attached optionally via a spacer, wherein said GLP-1 compound is present in a concentration from 0.1 mg/ml to 100 mg/ml, and wherein said formulation has a pH from 7.0 to 10.

In a further aspect the present invention relates to a method of reducing blood glucose levels, treating diabetes type I, diabetes type II, obesity, or inhibiting gastric acid secretion, inhibiting apoptosis of β-cells, or stimulating the proliferation of β-cells comprising administering to a patient in need thereof an effective amount of a pharmaceutical formulation comprising an aqueous solution of a GLP-1 compound, and a buffer, wherein said GLP-1 compound is GLP-1(7-37) or an analogue thereof wherein an amino acid residue of the parent peptide has a lipophilic substituent attached optionally via a spacer, wherein said GLP-1 compound is present in a concentration from 1 mg/ml to 100 mg/ml, and wherein said formulation has a pH from 7.0 to 10.

In a further aspect the present invention relates to a method of treating gastric ulcers comprising administering to a patient in need thereof an effective amount of a pharmaceutical formulation comprising an aqueous solution of a GLP-1 compound, and a buffer, wherein said GLP-1 compound is GLP-1(7-37) or an analogue thereof wherein an amino acid residue of the parent peptide has a lipophilic substituent attached optionally via a spacer, wherein said GLP-1 compound is present in a concentration from 0.1 mg/ml to 100 mg/ml, and wherein said formulation has a pH from 7.0 to 10.

In a further aspect the present invention relates to a method of treating gastric ulcers comprising administering to a patient in need thereof an effective amount of a pharmaceutical formulation comprising an aqueous solution of a GLP-1 compound, and a buffer, wherein said GLP-1 compound is GLP-1(7-37) or an analogue thereof wherein an amino acid residue of the parent peptide has a lipophilic substituent attached optionally via a spacer, wherein said GLP-1 compound is present in a concentration from 1 mg/ml to 100 mg/ml, and wherein said formulation has a pH from 7.0 to 10.

In a further aspect the present invention relates to a method of treating myocardial infarct comprising administering to a patient in need thereof an effective amount of a pharmaceutical formulation comprising an aqueous solution of a GLP-1 compound, and a buffer, wherein said GLP-1 compound is GLP-1(7-37) or an analogue thereof wherein an amino acid residue of the parent peptide has a lipophilic substituent attached optionally via a spacer, wherein said GLP-1 compound is present in a concentration from 0.1 mg/ml to 100 mg/ml, and wherein said formulation has a pH from 7.0 to 10.

In a further aspect the present invention relates to a method of treating myocardial infarct comprising administering to a patient in need thereof an effective amount of a pharmaceutical formulation comprising an aqueous solution of a GLP-1 compound, and a buffer, wherein said GLP-1 compound is GLP-1(7-37) or an analogue thereof wherein an amino acid residue of the parent peptide has a lipophilic substituent attached optionally via a spacer, wherein said GLP-1 compound is present in a concentration from 1 mg/ml to 100 mg/ml, and wherein said formulation has a pH from 7.0 to 10.

In a further aspect the present invention relates to a method of treating impaired glucose tolerance (IGT) comprising administering to a patient in need thereof an effective amount of a pharmaceutical formulation comprising an aqueous solution of a GLP-1 compound, and a buffer, wherein said GLP-1 compound is GLP-1(7-37) or an analogue thereof wherein an amino acid residue of the parent peptide has a lipophilic substituent attached optionally via a spacer, wherein said GLP-1 compound is present in a concentration from 0.1 mg/ml to 100 mg/ml, and wherein said formulation has a pH from 7.0 to 10.

In a further aspect the present invention relates to a method of treating impaired glucose tolerance (IGT) comprising administering to a patient in need thereof an effective amount of a pharmaceutical formulation comprising an aqueous solution of a GLP-1 compound, and a buffer, wherein said GLP-1 compound is GLP-1(7-37) or an analogue thereof wherein an amino acid residue of the parent peptide has a lipophilic substituent attached optionally via a spacer, wherein said GLP-1 compound is present in a concentration from 1 mg/ml to 100 mg/ml, and wherein said formulation has a pH from 7.0 to 10.

In a further aspect the present invention relates to a method of reducing body weight in a subject in need of body weight reduction comprising administering to the subject an effective amount sufficient to cause reduction in body weight for a period of time effective to produce weight loss, said time being at least 4 weeks, of a pharmaceutical formulation comprising an aqueous solution of a GLP-1 compound, and a buffer, wherein said GLP-1 compound is GLP-1(7-37) or an analogue thereof wherein an amino acid residue of the parent peptide has a lipophilic substituent attached optionally via a spacer, wherein said GLP-1 compound is present in a concentration from 0.1 mg/ml to 100 mg/ml, and wherein said formulation has a pH from 7.0 to 10.

In a further aspect the present invention relates to a method of reducing body weight in a subject in need of body weight reduction comprising administering to the subject an effective amount sufficient to cause reduction in body weight for a period of time effective to produce weight loss, said time being at least 4 weeks, of a pharmaceutical formulation comprising an aqueous solution of a GLP-1 compound, and a buffer, wherein said GLP-1 compound is GLP-1(7-37) or an analogue thereof wherein an amino acid residue of the parent peptide has a lipophilic substituent attached optionally via a spacer, wherein said GLP-1 compound is present in a concentration from 1 mg/ml to 100 mg/ml, and wherein said formulation has a pH from 7.0 to 10.

In a further aspect the present invention relates to a method of treating dyslipidemia, stroke, left ventricular hypertrophy, arrhythmia, bacteraemia, septicaemia, irritable bowel disease, functional dyspepsia, comprising administering to a patient in need thereof an effective amount of a pharmaceutical formulation comprising an aqueous solution of a GLP-1 compound, and a buffer, wherein said GLP-1 compound is GLP-1(7-37) or an analogue thereof wherein an amino acid residue of the parent peptide has a lipophilic substituent attached optionally via a spacer, wherein said GLP-1 compound is present in a concentration from 0.1 mg/ml to 100 mg/ml, and wherein said formulation has a pH from 7.0 to 10.

In a further aspect the present invention relates to a method of treating dyslipidemia, stroke, left ventricular hypertrophy, arrhythmia, bacteraemia, septicaemia, irritable bowel disease, functional dyspepsia, comprising administering to a patient in need thereof an effective amount of a pharmaceutical formulation comprising an aqueous solution of a GLP-1 compound, and a buffer, wherein said GLP-1 compound is GLP-1(7-37) or an analogue thereof wherein an amino acid residue of the parent peptide has a lipophilic substituent attached optionally via a spacer, wherein said GLP-1 compound is present in a concentration from 1 mg/ml to 100 mg/ml, and wherein said formulation has a pH from 7.0 to 10.

The term "an effective amount" is the effective dose to be determined by a qualified practitioner, who may titrate dosages to achieve the desired response. Factors for consideration of dose will include potency, bioavailability, desired pharmacokinetic/pharmacodynamic profiles, condition of treatment (e.g. diabetes, obesity, weight loss, gastric ulcers), patient-related factors (e.g. weight, health, age, etc.), presence of co-administered medications (e.g. insulin), time of administration, or other factors known to a medical practitioner.

In a further aspect the present invention relates to use of a GLP-1 compound for the preparation of a pharmaceutical formulation comprising an aqueous solution of the GLP-1 compound, and a buffer, wherein said GLP-1 compound is GLP-1(7-37) or an analogue thereof wherein an amino acid residue of the parent peptide has a lipophilic substituent attached optionally via a spacer, wherein said GLP-1 compound is present in a concentration from 0.1 mg/ml to 100 mg/ml, and wherein said formulation has a pH from 7.0 to 10, for reducing blood glucose levels.

In a further aspect the present invention relates to use of a GLP-1 compound for the preparation of a pharmaceutical formulation comprising an aqueous solution of the GLP-1 compound, and a buffer, wherein said GLP-1 compound is GLP-1(7-37) or an analogue thereof wherein an amino acid residue of the parent peptide has a lipophilic substituent attached optionally via a spacer, wherein said GLP-1 compound is present in a concentration from 1 mg/ml to 100 mg/ml, and wherein said formulation has a pH from 7.0 to 10, for reducing blood glucose levels.

In a further aspect the present invention relates to use of a GLP-1 compound for the preparation of a pharmaceutical formulation comprising an aqueous solution of the GLP-1 compound, and a buffer, wherein said GLP-1 compound is GLP-1(7-37) or an analogue thereof wherein an amino acid residue of the parent peptide has a lipophilic substituent attached optionally via a spacer, wherein said GLP-1 compound is present in a concentration from 0.1 mg/ml to 100 mg/ml, and wherein said formulation has a pH from 7.0 to 10, for treating diabetes type I.

In a further aspect the present invention relates to use of a GLP-1 compound for the preparation of a pharmaceutical formulation comprising an aqueous solution of the GLP-1 compound, and a buffer, wherein said GLP-1 compound is GLP-1(7-37) or an analogue thereof wherein an amino acid residue of the parent peptide has a lipophilic substituent attached optionally via a spacer, wherein said GLP-1 compound is present in a concentration from 1 mg/ml to 100 mg/ml, and wherein said formulation has a pH from 7.0 to 10, for treating diabetes type I.

In a further aspect the present invention relates to use of a GLP-1 compound for the preparation of a pharmaceutical formulation comprising an aqueous solution of the GLP-1 compound, and a buffer, wherein said GLP-1 compound is GLP-1(7-37) or an analogue thereof wherein an amino acid residue of the parent peptide has a lipophilic substituent attached optionally via a spacer, wherein said GLP-1 compound is present in a concentration from 0.1 mg/ml to 100 mg/ml, and wherein said formulation has a pH from 7.0 to 10, for treating diabetes type II.

In a further aspect the present invention relates to use of a GLP-1 compound for the preparation of a pharmaceutical formulation comprising an aqueous solution of the GLP-1 compound, and a buffer, wherein said GLP-1 compound is GLP-1(7-37) or an analogue thereof wherein an amino acid residue of the parent peptide has a lipophilic substituent attached optionally via a spacer, wherein said GLP-1 compound is present in a concentration from 1 mg/ml to 100 mg/ml, and wherein said formulation has a pH from 7.0 to 10, for treating diabetes type II.

In a further aspect the present invention relates to use of a GLP-1 compound for the preparation of a pharmaceutical formulation comprising an aqueous solution of the GLP-1 compound, and a buffer, wherein said GLP-1 compound is GLP-1(7-37) or an analogue thereof wherein an amino acid residue of the parent peptide has a lipophilic substituent attached optionally via a spacer, wherein said GLP-1 compound is present in a concentration from 0.1 mg/ml to 100 mg/ml, and wherein said formulation has a pH from 7.0 to 10, for treating obesity.

In a further aspect the present invention relates to use of a GLP-1 compound for the preparation of a pharmaceutical formulation comprising an aqueous solution of the GLP-1 compound, and a buffer, wherein said GLP-1 compound is GLP-1(7-37) or an analogue thereof wherein an amino acid residue of the parent peptide has a lipophilic substituent attached optionally via a spacer, wherein said GLP-1 compound is present in a concentration from 1 mg/ml to 100 mg/ml, and wherein said formulation has a pH from 7.0 to 10, for treating obesity.

In a further aspect the present invention relates to use of a GLP-1 compound for the preparation of a pharmaceutical formulation comprising an aqueous solution of the GLP-1 compound, and a buffer, wherein said GLP-1 compound is GLP-1(7-37) or an analogue thereof wherein an amino acid residue of the parent peptide has a lipophilic substituent attached optionally via a spacer, wherein said GLP-1 compound is present in a concentration from 0.1 mg/ml to 100 mg/ml, and wherein said formulation has a pH from 7.0 to 10, for reducing body weight, typically for reducing body weight in a type 2 diabetic subject.

In a further aspect the present invention relates to use of a GLP-1 compound for the preparation of a pharmaceutical formulation comprising an aqueous solution of the GLP-1 compound, and a buffer, wherein said GLP-1 compound is GLP-1(7-37) or an analogue thereof wherein an amino acid residue of the parent peptide has a lipophilic substituent attached optionally via a spacer, wherein said GLP-1 compound is present in a concentration from 1 mg/ml to 100 mg/ml, and wherein said formulation has a pH from 7.0 to 10, for reducing body weight, typically for reducing body weight in a type 2 diabetic subject.

In a further aspect the present invention relates to use of a GLP-1 compound for the preparation of a pharmaceutical formulation comprising an aqueous solution of the GLP-1 compound, and a buffer, wherein said GLP-1 compound is GLP-1(7-37) or an analogue thereof wherein an amino acid residue of the parent peptide has a lipophilic substituent attached optionally via a spacer, wherein said GLP-1 compound is present in a concentration from 0.1 mg/ml to 100 mg/ml, and wherein said formulation has a pH from 7.0 to 10, for treating gastric ulcers.

In a further aspect the present invention relates to use of a GLP-1 compound for the preparation of a pharmaceutical formulation comprising an aqueous solution of the GLP-1 compound, and a buffer, wherein said GLP-1 compound is GLP-1(7-37) or an analogue thereof wherein an amino acid residue of the parent peptide has a lipophilic substituent attached optionally via a spacer, wherein said GLP-1 compound is present in a concentration from 1 mg/ml to 100 mg/ml, and wherein said formulation has a pH from 7.0 to 10, for treating gastric ulcers.

In a further aspect the present invention relates to use of a GLP-1 compound for the preparation of a pharmaceutical formulation comprising an aqueous solution of the GLP-1 compound, and a buffer, wherein said GLP-1 compound is GLP-1(7-37) or an analogue thereof wherein an amino acid residue of the parent peptide has a lipophilic substituent attached optionally via a spacer, wherein said GLP-1 compound is present in a concentration from 0.1 mg/ml to 100 mg/ml, and wherein said formulation has a pH from 7.0 to 10, for inhibition of apoptosis of β-cells.

In a further aspect the present invention relates to use of a GLP-1 compound for the preparation of a pharmaceutical formulation comprising an aqueous solution of the GLP-1 compound, and a buffer, wherein said GLP-1 compound is GLP-1(7-37) or an analogue thereof wherein an amino acid residue of the parent peptide has a lipophilic substituent attached optionally via a spacer, wherein said GLP-1 compound is present in a concentration from 1 mg/ml to 100 mg/ml, and wherein said formulation has a pH from 7.0 to 10, for inhibition of apoptosis of β-cells.

The term "treatment" is defined as the management and care of a patient, e.g. a mammal, in particular a human, for the purpose of combating the disease, condition, or disorder and includes the administration of a GLP-1 compound to prevent the onset of the symptoms or complications, or alleviating the symptoms or complications, or eliminating the disease, condition, or disorder. Pharmaceutical compositions containing a GLP-1 compound according to the present invention may be administered parenterally to patients in need of such a treatment. Parenteral administration may be performed by subcutaneous, intramuscular or intravenous injection by means of a syringe, optionally a pen-like syringe. Alternatively, parenteral administration can be performed by means of an infusion pump. A further option is a composition which may be a solution or suspension for the administration of the GLP-1 compound in the form of a nasal or pulmonal spray. As a still further option, the pharmaceutical compositions containing the GLP-1 compound of the invention can also be adapted to transdermal administration, e.g. from a patch, optionally a iontophoretic patch, or transmucosal, e.g. bucal, administration.

A pharmaceutical formulation is found to be physically unstable when it exhibits turbidity. A pharmaceutical formulation of GLP1(7-37) is found to be physically unstable as it turns out to be turbid momentaneously after preparation, whereas the same pharmaceutical formulation comprising a GLP-1 compound, for example $Arg^{34}$, $Lys^{26}$(N-ε-(γ-Glu(N-α-hexadecanoyl)))-GLP-1(7-37), is found to be physically stable for more than 90 days at 5° C. Some of the present formulations are physically stable for more than 11 months and for more than 22 months at 5° C.

Physical stability of the formulations is evaluated by means of visual inspection and turbidity after storage of the formulation at different temperatures in top filled glass cartridges for various time periods. Visual inspection of the formulations is performed in a sharp focused light with a dark background. The turbidity of the formulation is characterized by a visual score ranking the degree of turbidity from 0 to 3 (a formulation showing no turbidity corresponds to a visual score 0, and a formulation showing visual turbidity in daylight corresponds to visual score 3). A formulation is classified physical unstable with respect to protein aggregation, when it shows visual turbidity in daylight.

In one embodiment of the invention the pharmaceutical formulation comprising the GLP-1 compound is physically stable for more than 12 weeks and for more than 15 months at 5° C. as measured by visual inspection.

In another embodiment of the invention the pharmaceutical formulation comprising the GLP-1 compound is physically stable for more than 12 weeks at 25° C. as measured by visual inspection.

In a further embodiment of the invention the pharmaceutical formulation comprising the GLP-1 compound is physically stable for more than 12 weeks at 37° C. as measured by visual inspection.

In another embodiment of the invention the formulation has a pH in the range from 7.5 to 10. In another embodiment of the invention the formulation has a pH in the range from 7.5 to 9.5. In a further embodiment of the invention the formulation has a pH in the range from 7.0 to 9.5. In a further embodiment of the invention the formulation has a pH in the range from 7.0 to 8.0. In a further embodiment of the invention the formulation has a pH in the range from 7.5 to 8.0. In a further embodiment of the invention the formulation has a pH in the range from 9.0 to 10.

In a further embodiment of the invention the buffer is selected from the group consisting of sodium acetate, sodium carbonate, citrate, glycylglycine, histidine, glycine, lysine, arginin, sodium dihydrogen phosphate, disodium hydrogen phosphate, sodium phosphate, and tris(hydroxymethyl)-aminomethan, or mixtures thereof. Each one of these specific buffers constitutes an alternative embodiment of the invention. In a preferred embodiment of the invention the buffer is glycylglycine, sodium dihydrogen phosphate, disodium hydrogen phosphate, sodium phosphate or mixtures thereof.

In a further embodiment of the invention the GLP-1 compound is present in a concentration from 0.1 mg/ml to 80 mg/ml. In a further embodiment of the invention the GLP-1 compound is present in a concentration from 1 mg/ml to 80 mg/ml. In a further embodiment of the invention the GLP-1 compound is present in a concentration from 0.1 mg/ml to 50 mg/ml. In a further embodiment of the invention the GLP-1 compound is present in a concentration from 1 mg/ml to 50 mg/ml. In a further embodiment of the invention the GLP-1 compound is present in a concentration from 0.1 mg/ml to 20 mg/ml. In a further embodiment of the invention the GLP-1 compound is present in a concentration from 1 mg/ml to 20 mg/ml. In a further embodiment of the invention the GLP-1 compound is present in a concentration from 0.1 mg/ml to 10 mg/ml. In a further embodiment of the invention the GLP-1 compound is present in a concentration from 1 mg/ml to 10 mg/ml. In a further embodiment of the invention the GLP-1 compound is present in a concentration from 0.1-5 mg/ml. In a further embodiment of the invention the GLP-1 compound is present in a concentration from 1-5 mg/ml. In a further embodiment of the invention the GLP-1 compound is present in a concentration from 0.1-0.5 mg/ml. In a further embodiment of the invention the GLP-1 compound is present in a concentration from 0.6-1 mg/ml. Each one of these specific concentration ranges constitutes an alternative embodiment of the invention.

In a further embodiment of the invention the formulation further comprises a pharmaceutically acceptable preservative. In a further embodiment of the invention the preservative is selected from the group consisting of phenol, m-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, or mixtures thereof. Each one of these specific preservatives constitutes an alternative embodiment of the invention. In a preferred embodiment of the invention the preservative is phenol or m-cresol.

In a further embodiment of the invention the preservative is present in a concentration from 0.1 mg/ml to 20 mg/ml. In a further embodiment of the invention the preservative is present in a concentration from 0.1 mg/ml to 5 mg/ml. In a further embodiment of the invention the preservative is present in a concentration from 5 mg/ml to 10 mg/ml. In a further embodiment of the invention the preservative is present in a concentration from 10 mg/ml to 20 mg/ml. Each one of these specific concentration ranges constitutes an alternative embodiment of the invention.

The use of a preservative in pharmaceutical compositions is well-known to the skilled person. For convenience reference is made to Remington: *The Science and Practice of Pharmacy,* $19^{th}$ edition, 1995.

In a further embodiment of the invention the formulation further comprises an isotonic agent. In a further embodiment of the invention the isotonic agent is selected from the group consisting of a salt (e.g. sodium chloride), a polyhydric alcohol (e.g. propyleneglycol, xylitol, mannitol, sorbitol or glycerol), a monosaccharide (e.g. glucose or maltose), a disaccharide (e.g. sucrose), an amino acid (e.g. L-glycine, L-histidine, arginine, lysine, isoleucine, aspartic acid, tryptophan, threonine), polyethyleneglycol (e.g. PEG400), or mixtures thereof. In a further embodiment of the invention the isotonic agent is selected from the group consisting of sodium chloride, glycerol, mannitol, glucose, sucrose, L-glycine, L-histidine, arginine, lysine or mixtures thereof. Each one of these specific isotonic agents constitutes an alternative embodiment of the invention. In a preferred embodiments of the invention the isotonic agent is mannitol or glycerol.

In a further embodiment of the invention the isotonic agent is present in a concentration from 1 mg/ml to 50 mg/ml. In a further embodiment of the invention the isotonic agent is present in a concentration from 1 mg/ml to 7 mg/ml. In a further embodiment of the invention the isotonic agent is present in a concentration from 8 mg/ml to 16 mg/ml. In a further embodiment of the invention the isotonic agent is present in a concentration from 17 mg/ml to 50 mg/ml. Each one of these specific concentration ranges constitutes an alternative embodiment of the invention.

The use of an isotonic agent in pharmaceutical compositions is well-known to the skilled person. For convenience reference is made to Remington: *The Science and Practice of Pharmacy*, 19$^{th}$ edition, 1995.

In a further embodiment of the invention the formulation further comprises a chelating agent. In a further embodiment of the invention the chelating agent is selected from salts of ethlenediaminetetraacetic acid (EDTA), citric acid, and aspartic acid, and mixtures thereof. Each one of these specific chelating agents constitutes an alternative embodiment of the invention.

In a further embodiment of the invention the chelating agent is present in a concentration from 0.1 mg/ml to 5 mg/ml. In a further embodiment of the invention the chelating agent is present in a concentration from 0.1 mg/ml to 2 mg/ml. In a further embodiment of the invention the chelating agent is present in a concentration from 2 mg/ml to 5 mg/ml.

The use of a chelating agent in pharmaceutical compositions is well-known to the skilled person. For convenience reference is made to Remington: *The Science and Practice of Pharmacy*, 19$^{th}$ edition, 1995.

In a further embodiment of the invention the formulation further comprises a stabiliser selected from the group of high molecular weight polymers or low molecular compounds. In a further embodiment of the invention the stabilizer is selected from polyethylene glycol (e.g. PEG 3350), polyvinylalcohol (PVA), polyvinylpyrrolidone, carboxymethylcellulose, different salts (e.g. sodium chloride), L-glycine, L-histidine, imidazole, arginine, lysine, isoleucine, aspartic acid, tryptophan, threonine and mixtures thereof. Each one of these specific stabilizers constitutes an alternative embodiment of the invention. In a preferred embodiment of the invention the stabiliser is selected from the group consisting of L-histidine, imidazole and arginine.

In a further embodiment of the invention the high molecular weight polymer is present in a concentration from 0.1 mg/ml to 50 mg/ml. In a further embodiment of the invention the high molecular weight polymer is present in a concentration from 0.1 mg/ml to 5 mg/ml. In a further embodiment of the invention the high molecular weight polymer is present in a concentration from 5 mg/ml to 10 mg/ml. In a further embodiment of the invention the high molecular weight polymer is present in a concentration from 10 mg/ml to 20 mg/ml. In a further embodiment of the invention the high molecular weight polymer is present in a concentration from 20 mg/ml to 30 mg/ml. In a further embodiment of the invention the high molecular weight polymer is present in a concentration from 30 mg/ml to 50 mg/ml.

In a further embodiment of the invention the low molecular weight compound is present in a concentration from 0.1 mg/ml to 50 mg/ml. In a further embodiment of the invention the low molecular weight compound is present in a concentration from 0.1 mg/ml to 5 mg/ml. In a further embodiment of the invention the low molecular weight compound is present in a concentration from 5 mg/ml to 10 mg/ml. In a further embodiment of the invention the low molecular weight compound is present in a concentration from 10 mg/ml to 20 mg/ml. In a further embodiment of the invention the low molecular weight compound is present in a concentration from 20 mg/ml to 30 mg/ml. In a further embodiment of the invention the low molecular weight compound is present in a concentration from 30 mg/ml to 50 mg/ml.

The use of a stabilizer in pharmaceutical compositions is well-known to the skilled person. For convenience reference is made to Remington: *The Science and Practice of Pharmacy*, 19$^{th}$ edition, 1995.

In a further embodiment of the invention the formulation further comprises a surfactant. In a further embodiment of the invention the surfactant is selected from a detergent, ethoxylated castor oil, polyglycolyzed glycerides, acetylated monoglycerides, sorbitan fatty acid esters, poloxamers, such as 188 and 407, polyoxyethylene sorbitan fatty acid esters, polyoxyethylene derivatives such as alkylated and alkoxylated derivatives (tweens, e.g. Tween-20, or Tween-80), monoglycerides or ethoxylated derivatives thereof, diglycerides or polyoxyethylene derivatives thereof, glycerol, cholic acid or derivatives thereof, lecithins, alcohols and phospholipids, glycerophospholipids (lecithins, kephalins, phosphatidyl serine), glyceroglycolipids (galactopyransoide), sphingophospholipids (sphingomyelin), and sphingoglycolipids (ceramides, gangliosides), DSS (docusate sodium, CAS registry no [577-11-7]), docusate calcium, CAS registry no [128-49-4]), docusate potassium, CAS registry no [7491-09-0]), SDS (sodium dodecyl sulfate or sodium lauryl sulfate), dipalmitoyl phosphatidic acid, sodium caprylate, bile acids and salts thereof and glycine or taurine conjugates, ursodeoxycholic acid, sodium cholate, sodium deoxycholate, sodium taurocholate, sodium glycocholate, N-Hexadecyl-N, N-dimethyl-3-ammonio-1-propanesulfonate, anionic (alkyl-aryl-sulphonates) monovalent surfactants, palmitoyl lysophosphatidyl-L-serine, lysophospholipids (e.g. 1-acyl-sn-glycero-3-phosphate esters of ethanolamine, choline, serine or threonine), alkyl, alkoxyl (alkyl ester), alkoxy (alkyl ether)-derivatives of lysophosphatidyl and phosphatidylcholines, e.g. lauroyl and myristoyl derivatives of lysophosphatidylcholine, dipalmitoylphosphatidylcholine, and modifications of the polar head group, that is cholines, ethanolamines, phosphatidic acid, serines, threonines, glycerol, inositol, and the positively charged DODAC, DOTMA, DCP, BISHOP, lysophosphatidylserine and lysophosphatidylthreonine, zwitterionic surfactants (e.g. N-alkyl-N,N-dimethylammonio-1-propanesulfonates, 3-cholamido-1-propyldimethylammonio-1-propanesulfonate, dodecylphosphocholine, myristoyl lysophosphatidylcholine, hen egg lysolecithin), cationic surfactants (quarternary ammonium bases) (e.g. cetyl-trimethylammonium bromide, cetylpyridinium chloride), non-ionic surfactants, polyethyleneoxide/polypropyleneoxide block copolymers (Pluronics/Tetronics, Triton X-100, Dodecyl β-D-glucopyranoside) or polymeric surfactants (Tween-40, Tween-80, Brij-35), fusidic acid derivatives—(e.g. sodium taurodihydrofusidate etc.), long-chain fatty acids and salts thereof C6-C12 (eg. oleic acid and caprylic acid), acylcarnitines and derivatives, $N^\alpha$-acylated derivatives of lysine, arginine or histidine, or side-chain acylated derivatives of lysine or arginine, $N^\alpha$-acylated derivatives of dipeptides comprising any combination of lysine, arginine or histidine and a neutral or acidic amino acid, $N^\alpha$-acylated derivative of a tripeptide comprising any combination of a neutral amino acid and two charged amino acids, or the surfactant may be selected from the group of imidazoline derivatives, or mixtures thereof. Each one of these specific surfactants constitutes an alternative embodiment of the invention.

The use of a surfactant in pharmaceutical compositions is well-known to the skilled person. For convenience reference is made to Remington: *The Science and Practice of Pharmacy*, 19$^{th}$ edition, 1995.

In a further embodiment of the invention the GLP-1 compound is selected from GLP-1(7-36) or an analogue thereof having a lysine residue wherein a lipophilic substituent optionally via a spacer is attached to the epsilon amino group of said lysine. In a further embodiment of the invention the GLP-1 compound is selected from a GLP-1(7-36) analogue having one lysine residue wherein one lipophilic substituent optionally via a spacer is attached to the epsilon amino group of said lysine. In a further embodiment of the invention the GLP-1 compound is selected from Arg26,34,Lys36GLP-1(7-36) having one lysine residue wherein one lipophilic substituent optionally via a spacer is attached to the epsilon amino group of said lysine.

In a further embodiment of the invention the GLP-1 compound is selected from GLP-1 (7-37) or an analogue thereof having a lysine residue wherein a lipophilic substituent optionally via a spacer is attached to the epsilon amino group of said lysine. In a further embodiment of the invention the GLP-1 compound is selected from a GLP-1(7-37) analogue having one lysine residue wherein one lipophilic substituent optionally via a spacer is attached to the epsilon amino group of said lysine. In a further embodiment of the invention the GLP-1 compound is selected from Arg34GLP-1(7-37), or Arg26GLP-1(7-37) having one lysine residue wherein one lipophilic substituent optionally via a spacer is attached to the epsilon amino group of said lysine.

In a further embodiment of the invention the GLP-1 compound is selected from GLP-1(7-38) or an analogue thereof having a lysine residue wherein a lipophilic substituent optionally via a spacer is attached to the epsilon amino group of said lysine. In a further embodiment of the invention the GLP-1 compound is selected from a GLP-1(7-38) analogue having one lysine residue wherein one lipophilic substituent optionally via a spacer is attached to the epsilon amino group of said lysine. In a further embodiment of the invention the GLP-1 compound is selected from Gly8, Arg26,34, Glu37, Lys38GLP-1(7-38) having one lysine residue wherein one lipophilic substituent optionally via a spacer is attached to the epsilon amino group of said lysine.

In a further embodiment of the invention the GLP-1 compound is selected from GLP-1(7-37) or an analogue thereof having one lipophilic substituent optionally attached via a spacer. In a further embodiment the lipophilic substituent is attached to any one of the amino acid residues in position 18-37, typically 26-34. In case of the GLP-1(7-36) analogue the lipophilic substituent is attached to any one of the amino acid residues in position 18-36, typically 26-34. In case of the GLP-1(7-38) analogue the lipophilic substituent is attached to any one of the amino acid residues in position 18-38, typically 26-34.

In the present text, the designation "an analogue" is used to designate a peptide wherein one or more amino acid residues of the parent peptide have been substituted by another amino acid residue and/or wherein one or more amino acid residues of the parent peptide have been deleted and/or wherein one or more amino acid residues have been added to the parent peptide. Such addition can take place either at the N-terminal end or at the C-terminal end of the parent peptide or both. Typically "GLP-1(7-37) or an analogue thereof" comprises GLP-1(7-36), GLP-1(7-37), and GLP-1(7-38), and analogues thereof wherein at least one, preferably at least 3, more preferable at least 5 amino acid residues have been substituted by another amino acid residue. In the present context the GLP-1 compound binds to a GLP-1 receptor, preferably with an affinity constant ($K_D$) or a potency ($EC_{50}$) of below 1 μM, e.g. below 100 nM (measured as known in the art, see e.g. WO 98/08871). The term "GLP-1 compound" encompasses GLP-1(7-37) and analogues thereof as well as derivatives of any of the foregoing. Derivatives of GLP-1 analogues are GLP-1 analogues which are chemically modified by introducing e.g. ester, alkyl or lipophilic functionalities on one or more amino acid residues of GLP-1 analogues. Methods for identifying GLP-1 compounds are described in WO 93/19175 (Novo Nordisk A/S). Examples of suitable GLP-1 compounds which can be used in the present formulation have been disclosed in e.g WO 98/08871, WO 99/43705, WO 99/43706, WO 99/43707, WO 99/43708, WO 99/43341, which are incorporated herein by reference.

The term "lipophilic substituent" is characterised by comprising 4-40 carbon atoms and having a solubility in water at 20° C. in the range from about 0.1 mg/100 ml water to about 250 mg/100 ml water, such as in the range from about 0.3 mg/100 ml water to about 75 mg/100 ml water. For instance, octanoic acid (C8) has a solubility in water at 20° C. of 68 mg/100 ml, decanoic acid (C10) has a solubility in water at 20° C. of 15 mg/100 ml, and octadecanoic acid (C18) has a solubility in water at 20° C. of 0.3 mg/100 ml.

The lipophilic substituent may be attached to an amino group of the GLP-1(7-37) or an analogue thereof by means of a carboxyl group of the lipophilic substituent which forms an amide bond with an amino group of the amino acid residue to which it is attached. Alternatively, the lipophilic substituent may be attached to said amino acid residue in such a way that an amino group of the lipophilic substituent forms an amide bond with a carboxyl group of the amino acid residue. As a further option, the lipophilic substituent may be linked to the GLP-1(7-37) or an analogue thereof via an ester bond. Formally, the ester can be formed either by reaction between a carboxyl group of the GLP-1(7-37) or an analogue thereof and a hydroxyl group of the substituent-to-be or by reaction between a hydroxyl group of the GLP-1(7-37) or an analogue thereof and a carboxyl group of the substituent-to-be. As a further alternative, the lipophilic substituent can be an alkyl group which is introduced into a primary amino group of the GLP-1(7-37) or an analogue thereof.

In a further alternative, the lipophilic substituent may be attached to the GLP-1(7-37) or an analogue thereof by means of a spacer in such a way that a carboxyl group of the spacer forms an amide bond with an amino group of the GLP-1(7-37) or an analogue thereof. A spacer must contain at least two functional groups, one to attach to a functional group of the lipophilic substituent and the other to a functional group of the parent GLP-1(7-37) or an analogue thereof. The term "spacer" is used in the present text to designate a bivalent moiety which contain at least two functional groups, one to attach to a functional group of the lipophilic substituent and the other to a functional group of the GLP-1 compound. Examples of suitable spacers are succinic acid, lysyl, glutamyl, asparagyl, glycyl, beta-alanyl and gamma-aminobutanoyl, or a dipeptide such as Gly-Lys, each of which constitutes an individual embodiment. When the spacer is succinic acid, one carboxyl group thereof may form an amide bond with an amino group of the amino acid residue, and the other carboxyl group thereof may form an amide bond with an amino group of the lipophilic substituent. When the spacer is lysyl, glutamyl, asparagyl, glycyl, beta-alanyl or gamma-aminobutanoyl, the carboxyl group thereof may form an amide bond with an amino group of the amino acid residue, and the amino group thereof may form an amide bond with a carboxyl group of the lipophilic substituent. When Lys is used as the spacer, a further spacer may in some instances be inserted between the ε-amino group of Lys and the lipophilic substituent. In one preferred embodiment, such a further spacer is succinic acid which forms an amide bond with the ε-amino group of Lys and with an amino group present in the lipophilic substituent. In another preferred embodiment such a further spacer is Glu or Asp which forms an amide bond with the ε-amino group of Lys and another amide bond with a carboxyl group present in the lipophilic substituent, that is, the lipophilic substituent is a $N^\epsilon$-acylated lysine residue. In an embodiment, the spacer is an amino acid residue except Cys or Met, or a dipeptide such as Gly-Lys. For purposes of the present invention, the phrase "a dipeptide such as Gly-Lys" means any combination of two amino acids except Cys or Met, typically a dipeptide wherein the C-terminal amino acid residue is Lys, His or Trp, typically Lys, and the N-terminal amino acid residue is Ala, Arg, Asp, Asn, Gly, Glu, Gln, Ile, Leu, Val, Phe, Pro, Ser, Tyr, Thr, Lys, His and Trp. Typically, an amino group of the GLP-1 compound forms an amide bond with a carboxylic group of the amino acid residue or dipeptide spacer, and an amino group of the amino acid residue or dipeptide spacer forms an amide bond with a carboxyl group of the lipophilic substituent.

In a further embodiment of the invention the lipophilic substituent has from 8 to 40 carbon atoms. In a further embodiment of the invention the lipophilic substituent has from 10 to 24 carbon atoms. In a further embodiment of the invention the lipophilic substituent has from 12 to 24 carbon atoms. In a further embodiment of the invention the lipophilic substituent has from 12 to 18 carbon atoms. In a further embodiment of the invention the lipophilic substituent has from 14 to 18 carbon atoms.

In a further embodiment of the invention the spacer is present. In a further embodiment of the invention the spacer is selected from an amino acid. In a further embodiment of the invention, the spacer is an amino acid residue except Cys or Met. In another embodiment, the spacer is a dipeptide such as Gly-Lys. In a further embodiment the spacer is selected from lysyl, glutamyl, asparagyl, glycyl, beta-alanyl and gamma-aminobutanoyl, each of which constitutes an individual embodiment. Typically used spacers are glutamyl, aminobutyroyl, and beta-alanyl (beta-Ala).

In another embodiment, the spacer is an unbranched alkane α,ω-dicarboxylic acid group having from 1 to 7 methylene groups, which spacer forms a bridge between an amino group of the parent peptide and an amino group of the lipophilic substituent. Typically, the spacer is succinic acid.

The lipophilic substituent(s) contain a functional group which can be attached to one of the following functional groups of an amino acid of the parent GLP-1(7-37) or an analogue thereof:

(a) the amino group attached to the alpha-carbon of the N-terminal amino acid,
(b) the carboxy group attached to the alpha-carbon of the C-terminal amino acid,
(c) the epsilon-amino group of any Lys residue,
(d) the carboxy group of the R group of any Asp and Glu residue,
(e) the hydroxy group of the R group of any Tyr, Ser and Thr residue,
(f) the amino group of the R group of any Trp, Asn, Gln, Arg, and His residue, or
(g) the thiol group of the R group of any Cys residue.

In a further embodiment of the invention, the lipophilic substituent is attached to the carboxy group of the R group of any Asp and Glu residue.

In a further embodiment of the invention, a lipophilic substituent is attached to the carboxy group attached to the alpha-carbon of the C-terminal amino acid.

In a further embodiment of the invention, a lipophilic substituent is attached to the epsilon-amino group of any Lys residue.

Each lipophilic substituent contains a functional group which may be attached to a functional group of an amino acid of the parent GLP-1(7-37) or an analogue thereof. For example, a lipophilic substituent may contain a carboxyl group which can be attached to an amino group of the parent GLP-1(7-37) or an analogue thereof by means of an amide bond.

In a further embodiment of the invention, the lipophilic substituent comprises a partially or completely hydrogenated cyclopentanophenathrene skeleton.

In a further embodiment of the invention, the lipophilic substituent is a straight chain or branched alkyl group.

In a further embodiment of the invention, the lipophilic substituent is an acyl group of a straight-chain or branched fatty acid.

In a further embodiment of the invention the lipophilic substituent is an acyl group having the formula $CH_3(CH_2)_nCO—$, wherein n is an integer from 4 to 38. In a further embodiment n is an integer from 12 to 38. In further embodiments the lipophilic substituent is selected from the following individual embodiments $CH_3(CH_2)_{12}CO—$, $CH_3(CH_2)_{14}CO—$, $CH_3(CH_2)_{16}CO—$, $CH_3(CH_2)_{18}CO—$, $CH_3(CH_2)_{20}CO—$ and $CH_3(CH_2)_{22}CO—$. In a specific embodiment, the lipophilic substituent is tetradecanoyl. In another specific embodiment, the lipophilic substituent is hexadecanoyl.

In another embodiment of the present invention, the lipophilic substituent has a group which is negatively charged such as a carboxylic acid group. For example, the lipophilic substituent may be an acyl group of a straight-chain or branched alkane α,ω-dicarboxylic acid of the formula $HOOC(CH_2)_mCO—$, wherein m is an integer from 4 to 38, preferably an integer from 12 to 38, and most preferably is $HOOC(CH_2)_{14}CO—$, $HOOC(CH_2)_{16}CO—$, $HOOC(CH_2)_{18}CO—$, $HOOC(CH_2)_{20}CO—$ or $HOOC(CH_2)_{22}CO—$.

In a further embodiment of the invention the GLP-1 compound is $Arg^{26,34},Lys^{36}$-(N-epsilon-(gamma-L-glutamyl(N-alfa-hexadecanoyl)))-GLP-1 (7-36).

In a further embodiment of the invention the GLP-1 compound is $Arg^{26},Lys^{34}$-(N-epsilon-(gamma-L-glutamyl(N-alfa-hexadecanoyl)))-GLP-1 (7-37).

In a further embodiment of the invention the GLP-1 compound is $Gly^8,Arg^{26,34},Glu^{37},Lys^{38}$-(N-epsilon-(gamma-L-glutamyl(N-alfa-hexadecanoyl)))-GLP-1 (7-38).

In a further embodiment of the invention the GLP-1 compound is $Arg^{34},Lys^{26}$-(N-epsilon-(gamma-aminobutyroyl(N-gamma-hexadecanoyl)))-GLP-1 (7-37).

In a further embodiment of the invention the GLP-1 compound is $Arg^{34},Lys^{26}$-(N-epsilon-(beta-alanyl(N-beta-hexadecanoyl)))-GLP-1 (7-37).

In a further embodiment of the invention the GLP-1 compound is $Arg^{34},Lys^{26}$-(N-epsilon-(beta-alanyl-(N-beta-tetradecanoyl)))-GLP-1 (7-37).

In a further embodiment of the invention the GLP-1 compound is $Arg^{34},Lys^{26}$-(N-epsilon-(gamma-aminobutyroyl)-(N-gamma-tetradecanoyl))-GLP-1-(7-37).

In a further embodiment of the invention the GLP-1 compound is $Arg^{34},Lys^{26}$-(N-epsilon-(beta-alanyl-(N-beta-16-hydroxyhexadecanoyl)))-GLP-1(7-37).

In a further embodiment of the invention the GLP-1 compound is $Arg^{34}$, $Lys^{26}(N\text{-}\epsilon\text{-}(\gamma\text{-Glu}(N\text{-}\alpha\text{-hexadecanoyl})))$-GLP-1(7-37).

Typically the invention relates to a pharmaceutical formulation consisting of an aqueous solution of 1 mg/ml $Arg^{34}$, $Lys^{26}(N\text{-}\epsilon\text{-}(\gamma\text{-Glu}(N\text{-}\alpha\text{-hexadecanoyl})))$-GLP-1(7-37), disodium hydrogen phosphate, 36.9 mg/ml mannitol, and 5 mg/ml phenol, at pH 7.9.

Typically the invention relates to a pharmaceutical formulation consisting of an aqueous solution of 2 mg/ml $Arg^{34}$, $Lys^{26}(N\text{-}\epsilon\text{-}(\gamma\text{-Glu}(N\text{-}\alpha\text{-hexadecanoyl})))$-GLP-1(7-37), disodium hydrogen phosphate, 36.9 mg/ml mannitol, and 5 mg/ml phenol, at pH 7.9.

Typically the invention relates to a pharmaceutical formulation consisting of an aqueous solution of 3 mg/ml $Arg^{34}$, $Lys^{26}(N\text{-}\epsilon\text{-}(\gamma\text{-Glu}(N\text{-}\alpha\text{-hexadecanoyl})))$-GLP-1(7-37), disodium hydrogen phosphate, 36.9 mg/ml mannitol, and 5 mg/ml phenol, at pH 7.9.

Typically the invention relates to a pharmaceutical formulation consisting of an aqueous solution of 5 mg/ml $Arg^{34}$, $Lys^{26}(N\text{-}\epsilon\text{-}(\gamma\text{-Glu}(N\text{-}\alpha\text{-hexadecanoyl})))$-GLP-1(7-37), disodium hydrogen phosphate, 36.9 mg/ml mannitol, and 5 mg/ml phenol, at pH 7.9.

Typically the invention relates to a pharmaceutical formulation consisting of an aqueous solution of 7 mg/ml $Arg^{34}$, $Lys^{26}(N\text{-}\epsilon\text{-}(\gamma\text{-Glu}(N\text{-}\alpha\text{-hexadecanoyl})))$-GLP-1(7-37), disodium hydrogen phosphate, 36.9 mg/ml mannitol, and 5 mg/ml phenol, at pH 7.9.

Typically the invention relates to a pharmaceutical formulation consisting of an aqueous solution of 1 mg/ml $Arg^{34}$, $Lys^{26}(N\text{-}\epsilon\text{-}(\gamma\text{-Glu}(N\text{-}\alpha\text{-hexadecanoyl})))$-GLP-1(7-37), disodium hydrogen phosphate, 36.9 mg/ml mannitol, and 5 mg/ml phenol, at pH 8.1.

Typically the invention relates to a pharmaceutical formulation consisting of an aqueous solution of 2 mg/ml $Arg^{34}$, $Lys^{26}(N\text{-}\epsilon\text{-}(\gamma\text{-Glu}(N\text{-}\alpha\text{-hexadecanoyl})))$-GLP-1(7-37), disodium hydrogen phosphate, 36.9 mg/ml mannitol, and 5 mg/ml phenol, at pH 8.1.

Typically the invention relates to a pharmaceutical formulation consisting of an aqueous solution of 3 mg/ml $Arg^{34}$, $Lys^{26}(N\text{-}\epsilon\text{-}(\gamma\text{-Glu}(N\text{-}\alpha\text{-hexadecanoyl})))$-GLP-1(7-37), disodium hydrogen phosphate, 36.9 mg/ml mannitol, and 5 mg/ml phenol, at pH 8.1.

Typically the invention relates to a pharmaceutical formulation consisting of an aqueous solution of 5 mg/ml $Arg^{34}$, $Lys^{26}(N\text{-}\epsilon\text{-}(\gamma\text{-Glu}(N\text{-}\alpha\text{-hexadecanoyl})))$-GLP-1(7-37), disodium hydrogen phosphate, 36.9 mg/ml mannitol, and 5 mg/ml phenol, at pH 8.1.

Typically the invention relates to a pharmaceutical formulation consisting of an aqueous solution of 7 mg/ml $Arg^{34}$, $Lys^{26}(N\text{-}\epsilon\text{-}(\gamma\text{-Glu}(N\text{-}\alpha\text{-hexadecanoyl})))$-GLP-1(7-37), disodium hydrogen phosphate, 36.9 mg/ml mannitol, and 5 mg/ml phenol, at pH 8.1.

Typically the invention relates to a pharmaceutical formulation consisting of an aqueous solution of 1 mg/ml $Arg^{34}$, $Lys^{26}(N\text{-}\epsilon\text{-}(\gamma\text{-Glu}(N\text{-}\alpha\text{-hexadecanoyl})))$-GLP-1(7-37), disodium hydrogen phosphate, 36.9 mg/ml mannitol, 5 mg/ml phenol, and 1.55 mg/ml L-His, at pH 7.9

Typically the invention relates to a pharmaceutical formulation consisting of an aqueous solution of 2 mg/ml $Arg^{34}$, $Lys^{26}(N\text{-}\epsilon\text{-}(\gamma\text{-Glu}(N\text{-}\alpha\text{-hexadecanoyl})))$-GLP-1(7-37), disodium hydrogen phosphate, 36.9 mg/ml mannitol, 5 mg/ml phenol, and 1.55 mg/ml L-His, at pH 7.9.

Typically the invention relates to a pharmaceutical formulation consisting of an aqueous solution of 3 mg/ml $Arg^{34}$, $Lys^{26}(N\text{-}\epsilon\text{-}(\gamma\text{-Glu}(N\text{-}\alpha\text{-hexadecanoyl})))$-GLP-1(7-37), disodium hydrogen phosphate, 36.9 mg/ml mannitol, 5 mg/ml phenol, and 1.55 mg/ml L-His, at pH 7.9.

Typically the invention relates to a pharmaceutical formulation consisting of an aqueous solution of 5 mg/ml $Arg^{34}$, $Lys^{26}(N\text{-}\epsilon\text{-}(\gamma\text{-Glu}(N\text{-}\alpha\text{-hexadecanoyl})))$-GLP-1(7-37), disodium hydrogen phosphate, 36.9 mg/ml mannitol, 5 mg/ml phenol, and 1.55 mg/ml L-His, at pH 7.9.

Typically the invention relates to a pharmaceutical formulation consisting of an aqueous solution of 7 mg/ml $Arg^{34}$, $Lys^{26}(N\text{-}\epsilon\text{-}(\gamma\text{-Glu}(N\text{-}\alpha\text{-hexadecanoyl})))$-GLP-1(7-37), disodium hydrogen phosphate, 36.9 mg/ml mannitol, 5 mg/ml phenol, and 1.55 mg/ml L-His, at pH 7.9.

Typically the invention relates to a pharmaceutical formulation consisting of an aqueous solution of 1 mg/ml $Arg^{34}$, $Lys^{26}(N\text{-}\epsilon\text{-}(\gamma\text{-Glu}(N\text{-}\alpha\text{-hexadecanoyl})))$-GLP-1(7-37), disodium hydrogen phosphate, 36.9 mg/ml mannitol, 5 mg/ml phenol, and 1.55 mg/ml L-His, at pH 8.1.

Typically the invention relates to a pharmaceutical formulation consisting of an aqueous solution of 2 mg/ml $Arg^{34}$, $Lys^{26}(N\text{-}\epsilon\text{-}(\gamma\text{-Glu}(N\text{-}\alpha\text{-hexadecanoyl})))$-GLP-1(7-37), disodium hydrogen phosphate, 36.9 mg/ml mannitol, 5 mg/ml phenol, and 1.55 mg/ml L-His, at pH 8.1.

Typically the invention relates to a pharmaceutical formulation consisting of an aqueous solution of 3 mg/ml $Arg^{34}$, $Lys^{26}(N\text{-}\epsilon\text{-}(\gamma\text{-Glu}(N\text{-}\alpha\text{-hexadecanoyl})))$-GLP-1(7-37), disodium hydrogen phosphate, 36.9 mg/ml mannitol, 5 mg/ml phenol, and 1.55 mg/ml L-His, at pH 8.1.

Typically the invention relates to a pharmaceutical formulation consisting of an aqueous solution of 5 mg/ml $Arg^{34}$, $Lys^{26}(N\text{-}\epsilon\text{-}(\gamma\text{-Glu}(N\text{-}\alpha\text{-hexadecanoyl})))$-GLP-1(7-37), disodium hydrogen phosphate, 36.9 mg/ml mannitol, 5 mg/ml phenol, and 1.55 mg/ml L-His, at pH 8.1.

Typically the invention relates to a pharmaceutical formulation consisting of an aqueous solution of 7 mg/ml $Arg^{34}$, $Lys^{26}(N\text{-}\epsilon\text{-}(\gamma\text{-Glu}(N\text{-}\alpha\text{-hexadecanoyl})))$-GLP-1(7-37), disodium hydrogen phosphate, 36.9 mg/ml mannitol, 5 mg/ml phenol, and 1.55 mg/ml L-His, at pH 8.1.

Typically the invention relates to a pharmaceutical formulation consisting of an aqueous solution of 1 mg/ml $Arg^{34}$, $Lys^{26}(N\text{-}\epsilon\text{-}(\gamma\text{-Glu}(N\text{-}\alpha\text{-hexadecanoyl})))$-GLP-1(7-37), disodium hydrogen phosphate, 16.0 mg/ml glycerol, and 5 mg/ml phenol, at pH 7.9.

Typically the invention relates to a pharmaceutical formulation consisting of an aqueous solution of 2 mg/ml $Arg^{34}$, $Lys^{26}(N\text{-}\epsilon\text{-}(\gamma\text{-Glu}(N\text{-}\alpha\text{-hexadecanoyl})))$-GLP-1(7-37), disodium hydrogen phosphate, 16.0 mg/ml glycerol, and 5 mg/ml phenol, at pH 7.9.

Typically the invention relates to a pharmaceutical formulation consisting of an aqueous solution of 3 mg/ml $Arg^{34}$, $Lys^{26}(N\text{-}\epsilon\text{-}(\gamma\text{-Glu}(N\text{-}\alpha\text{-hexadecanoyl})))$-GLP-1(7-37), disodium hydrogen phosphate, 16.0 mg/ml glycerol, and 5 mg/ml phenol, at pH 7.9.

Typically the invention relates to a pharmaceutical formulation consisting of an aqueous solution of 1 mg/ml $Arg^{34}$, Lys$^{26}$(N-ε-(γ-Glu(N-α-hexadecanoyl)))-GLP-1(7-37), disodium hydrogen phosphate, 16.0 mg/ml glycerol, and 7 mg/ml phenol, at pH 7.9.

Typically the invention relates to a pharmaceutical formulation consisting of an aqueous solution of 2 mg/ml Arg$^{34}$, Lys$^{26}$(N-ε-(γ-Glu(N-α-hexadecanoyl)))-GLP-1(7-37), disodium hydrogen phosphate, 16.0 mg/ml glycerol, and 7 mg/ml phenol, at pH 7.9.

Typically the invention relates to a pharmaceutical formulation consisting of an aqueous solution of 3 mg/ml Arg$^{34}$, Lys$^{26}$(N-ε-(γ-Glu(N-α-hexadecanoyl)))-GLP-1(7-37), disodium hydrogen phosphate, 16.0 mg/ml glycerol, and 7 mg/ml phenol, at pH 7.9.

Typically the invention relates to a pharmaceutical formulation consisting of an aqueous solution of 5 mg/ml Arg$^{34}$, Lys$^{26}$(N-ε-(γ-Glu(N-α-hexadecanoyl)))-GLP-1(7-37), disodium hydrogen phosphate, 36.9 mg/ml mannitol, and 5 mg/ml phenol, at pH 7.9.

Typically the invention relates to a pharmaceutical formulation consisting of an aqueous solution of 1 mg/ml Arg$^{34}$, Lys$^{26}$(N-ε-(γ-Glu(N-α-hexadecanoyl)))-GLP-1(7-37), glycylglycine, 16.0 mg/ml glycerol, and 5 mg/ml phenol, at pH 7.9.

Typically the invention relates to a pharmaceutical formulation consisting of an aqueous solution of 2 mg/ml Arg$^{34}$, Lys$^{26}$(N-ε-(γ-Glu(N-α-hexadecanoyl)))-GLP-1(7-37), glycylglycine, 16.0 mg/ml glycerol, and 5 mg/ml phenol, at pH 7.9.

Typically the invention relates to a pharmaceutical formulation consisting of an aqueous solution of 3 mg/ml Arg$^{34}$, Lys$^{26}$(N-ε-(γ-Glu(N-α-hexadecanoyl)))-GLP-1(7-37), glycylglycine, 16.0 mg/ml glycerol, and 5 mg/ml phenol, at pH 7.9.

Typically the invention relates to a pharmaceutical formulation consisting of an aqueous solution of 1 mg/ml Arg$^{34}$, Lys$^{26}$(N-ε-(γ-Glu(N-α-hexadecanoyl)))-GLP-1(7-37), glycylglycine, 16.0 mg/ml glycerol, and 7 mg/ml phenol, at pH 7.9.

Typically the invention relates to a pharmaceutical formulation consisting of an aqueous solution of 2 mg/ml Arg$^{34}$, Lys$^{26}$(N-ε-(γ-Glu(N-α-hexadecanoyl)))-GLP-1(7-37), glycylglycine, 16.0 mg/ml glycerol, and 7 mg/ml phenol, at pH 7.9.

Typically the invention relates to a pharmaceutical formulation consisting of an aqueous solution of 3 mg/ml Arg$^{34}$, Lys$^{26}$(N-ε-(γ-Glu(N-α-hexadecanoyl)))-GLP-1(7-37), glycylglycine, 16.0 mg/ml glycerol, and 7 mg/ml phenol, at pH 7.9.

Typically the invention relates to a pharmaceutical formulation consisting of an aqueous solution of 1 mg/ml Arg$^{34}$, Lys$^{26}$(N-ε-(γ-Glu(N-α-hexadecanoyl)))-GLP-1(7-37), disodium hydrogen phosphate/sodium dihydrogen phosphate, 17.0 mg/ml mannitol, and 18 mg/ml benzylalcohol, at pH 7.0.

Typically the invention relates to a pharmaceutical formulation consisting of an aqueous solution of 2 mg/ml Arg$^{34}$, Lys$^{26}$(N-ε-(γ-Glu(N-α-hexadecanoyl)))-GLP-1(7-37), disodium hydrogen phosphate/sodium dihydrogen phosphate, 17.0 mg/ml mannitol, and 18 mg/ml benzylalcohol, at pH 7.0.

Typically the invention relates to a pharmaceutical formulation consisting of an aqueous solution of 3 mg/ml Arg$^{34}$, Lys$^{26}$(N-ε-(γ-Glu(N-α-hexadecanoyl)))-GLP-1(7-37), disodium hydrogen phosphate/sodium dihydrogen phosphate, 17.0 mg/ml mannitol, and 18 mg/ml benzylalcohol, at pH 7.0.

Typically the invention relates to a pharmaceutical formulation consisting of an aqueous solution of 5 mg/ml Arg$^{34}$, Lys$^{26}$(N-ε-(γ-Glu(N-α-hexadecanoyl)))-GLP-1(7-37), disodium hydrogen phosphate/sodium dihydrogen phosphate, 17.0 mg/ml mannitol, and 18 mg/ml benzylalcohol, at pH 7.0.

Typically the invention relates to a pharmaceutical formulation consisting of an aqueous solution of 1 mg/ml Arg$^{34}$, Lys$^{26}$(N-ε-(γ-Glu(N-α-hexadecanoyl)))-GLP-1(7-37), disodium hydrogen phosphate/sodium dihydrogen phosphate, 38.5 mg/ml mannitol, and either 3 mg/ml m-cresol or 1.5 mg/ml phenol, at pH 7.0.

Typically the invention relates to a pharmaceutical formulation consisting of an aqueous solution of 2 mg/ml Arg$^{34}$, Lys$^{26}$(N-ε-(γ-Glu(N-α-hexadecanoyl)))-GLP-1(7-37), disodium hydrogen phosphate/sodium dihydrogen phosphate, 38.5 mg/ml mannitol, and either 3 mg/ml m-cresol or 1.5 mg/ml phenol, at pH 7.0.

Typically the invention relates to a pharmaceutical formulation consisting of an aqueous solution of 3 mg/ml Arg$^{34}$, Lys$^{26}$(N-ε-(γ-Glu(N-α-hexadecanoyl)))-GLP-1(7-37), disodium hydrogen phosphate/sodium dihydrogen phosphate, 38.5 mg/ml mannitol, and either 3 mg/ml m-cresol or 1.5 mg/ml phenol, at pH 7.0.

Typically the invention relates to a pharmaceutical formulation consisting of an aqueous solution of 5 mg/ml Arg$^{34}$, Lys$^{26}$(N-ε-(γ-Glu(N-α-hexadecanoyl)))-GLP-1(7-37), disodium hydrogen phosphate/sodium dihydrogen phosphate, 38.5 mg/ml mannitol, and either 3 mg/ml m-cresol or 1.5 mg/ml phenol, at pH 7.0.

Typically the invention relates to a pharmaceutical formulation consisting of an aqueous solution of 1 mg/ml Arg$^{34}$, Lys$^{26}$(N-ε-(γ-Glu(N-α-hexadecanoyl)))-GLP-1(7-37), disodium hydrogen phosphate/sodium dihydrogen phosphate, 17.0 mg/ml mannitol, and 18 mg/ml benzylalcohol, at pH 7.8.

Typically the invention relates to a pharmaceutical formulation consisting of an aqueous solution of 2 mg/ml Arg$^{34}$, Lys$^{26}$(N-ε-(γ-Glu(N-α-hexadecanoyl)))-GLP-1(7-37), disodium hydrogen phosphate/sodium dihydrogen phosphate, 17.0 mg/ml mannitol, and 18 mg/ml benzylalcohol, at pH 7.8.

Typically the invention relates to a pharmaceutical formulation consisting of an aqueous solution of 3 mg/ml Arg$^{34}$, Lys$^{26}$(N-ε-(γ-Glu(N-α-hexadecanoyl)))-GLP-1(7-37), disodium hydrogen phosphate/sodium dihydrogen phosphate, 17.0 mg/ml mannitol, and 18 mg/ml benzylalcohol, at pH 7.8.

Typically the invention relates to a pharmaceutical formulation consisting of an aqueous solution of 5 mg/ml Arg$^{34}$, Lys$^{26}$(N-ε-(γ-Glu(N-α-hexadecanoyl)))-GLP-1(7-37), disodium hydrogen phosphate/sodium dihydrogen phosphate, 17.0 mg/ml mannitol, and 18 mg/ml benzylalcohol, at pH 7.8.

Typically the invention relates to a pharmaceutical formulation consisting of an aqueous solution of 1 mg/ml Arg$^{34}$, Lys$^{26}$(N-ε-(γ-Glu(N-α-hexadecanoyl)))-GLP-1(7-37), glycine, 36.9 mg/ml mannitol, and 5 mg/ml phenol, at pH 9.4.

Typically the invention relates to a pharmaceutical formulation consisting of an aqueous solution of 2 mg/ml Arg$^{34}$, Lys$^{26}$(N-ε-(γ-Glu(N-α-hexadecanoyl)))-GLP-1(7-37), glycine, 36.9 mg/ml mannitol, and 5 mg/ml phenol, at pH 9.4.

Typically the invention relates to a pharmaceutical formulation consisting of an aqueous solution of 3 mg/ml Arg$^{34}$, Lys$^{26}$(N-ε-(γ-Glu(N-α-hexadecanoyl)))-GLP-1(7-37), glycine, 36.9 mg/ml mannitol, and 5 mg/ml phenol, at pH 9.4.

Typically the invention relates to a pharmaceutical formulation consisting of an aqueous solution of 5 mg/ml Arg$^{34}$, Lys$^{26}$(N-ε-(γ-Glu(N-α-hexadecanoyl)))-GLP-1(7-37), glycine, 36.9 mg/ml mannitol, and 5 mg/ml phenol, at pH 9.4.

Typically the invention relates to a pharmaceutical formulation consisting of an aqueous solution of 1 mg/ml Arg$^{34}$, Lys$^{26}$(N-ε-(γ-Glu(N-α-hexadecanoyl)))-GLP-1(7-37), glycine, 36.9 mg/ml mannitol, 5 mg/ml phenol, and either 1 mg/ml EDTA or 1.55 mg/ml L-His, at pH 9.4.

Typically the invention relates to a pharmaceutical formulation consisting of an aqueous solution of 2 mg/ml Arg$^{34}$, Lys$^{26}$(N-ε-(γ-Glu(N-α-hexadecanoyl)))-GLP-1(7-37), glycine, 36.9 mg/ml mannitol, 5 mg/ml phenol, and 1 mg/ml EDTA/1.55 mg/ml L-His, at pH 9.4.

Typically the invention relates to a pharmaceutical formulation consisting of an aqueous solution of 1 mg/ml Arg$^{34}$, Lys$^{26}$(N-ε-(γ-Glu(N-α-hexadecanoyl)))-GLP-1(7-37), disodium hydrogen phosphate, 16.0 mg/ml glycerol, 5 mg/ml phenol, and 1.55 mg/ml L-His, at pH 7.4.

Typically the invention relates to a pharmaceutical formulation consisting of an aqueous solution of 2 mg/ml Arg$^{34}$, Lys$^{26}$(N-ε-(γ-Glu(N-α-hexadecanoyl)))-GLP-1(7-37), disodium hydrogen phosphate, 16.0 mg/ml glycerol, 5 mg/ml phenol, and 1.55 mg/ml L-His, at pH 7.4.

Typically the invention relates to a pharmaceutical formulation consisting of an aqueous solution of 5 mg/ml Arg$^{34}$, Lys$^{26}$(N-ε-(γ-Glu(N-α-hexadecanoyl)))-GLP-1(7-37), disodium hydrogen phosphate, 16.0 mg/ml glycerol, 5 mg/ml phenol, and 1.55 mg/ml L-His, at pH 7.4.

Typically the invention relates to a pharmaceutical formulation consisting of an aqueous solution of 1 mg/ml Arg$^{34}$, Lys$^{26}$(N-ε-(γ-Glu(N-α-hexadecanoyl)))-GLP-1(7-37), disodium hydrogen phosphate, 16.0 mg/ml glycerol, 7 mg/ml phenol, and 1.55 mg/ml L-His, at pH 7.4.

Typically the invention relates to a pharmaceutical formulation consisting of an aqueous solution of 2 mg/ml Arg$^{34}$, Lys$^{26}$(N-ε-(γ-Glu(N-α-hexadecanoyl)))-GLP-1(7-37), disodium hydrogen phosphate, 16.0 mg/ml glycerol, 7 mg/ml phenol, and 1.55 mg/ml L-His, at pH 7.4.

Typically the invention relates to a pharmaceutical formulation consisting of an aqueous solution of 5 mg/ml Arg$^{34}$, Lys$^{26}$(N-ε-(γ-Glu(N-α-hexadecanoyl)))-GLP-1(7-37), disodium hydrogen phosphate, 16.0 mg/ml glycerol, 7 mg/ml phenol, and 1.55 mg/ml L-His, at pH 7.4.

Typically the invention relates to a pharmaceutical formulation consisting of an aqueous solution of 3 mg/ml Arg$^{34}$, Lys$^{26}$(N-ε-(γ-Glu(N-α-hexadecanoyl)))-GLP-1(7-37), glycine, 36.9 mg/ml mannitol, 5 mg/ml phenol, and either 1 mg/ml EDTA or 1.55 mg/ml L-His, at pH 9.4.

Typically the invention relates to a pharmaceutical formulation consisting of an aqueous solution of 5 mg/ml Arg$^{34}$, Lys$^{26}$(N-ε-(γ-Glu(N-α-hexadecanoyl)))-GLP-1(7-37), glycine, 36.9 mg/ml mannitol, 5 mg/ml phenol, and either 1 mg/ml EDTA or 1.55 mg/ml L-His, at pH 9.4.

Typically the invention relates to a pharmaceutical formulation consisting of an aqueous solution of 1 mg/ml Arg$^{34}$, Lys$^{26}$(N-ε-(γ-Glu(N-α-hexadecanoyl)))-GLP-1(7-37), glycine, 36.9 mg/ml mannitol, 5 mg/ml phenol, and either 4 mg/ml Poloxamer 188 or 30 mg/ml PEG 35000, at pH 9.4.

Typically the invention relates to a pharmaceutical formulation consisting of an aqueous solution of 2 mg/ml Arg$^{34}$, Lys$^{26}$(N-ε-(γ-Glu(N-α-hexadecanoyl)))-GLP-1(7-37), glycine, 36.9 mg/ml mannitol, 5 mg/ml phenol, and either 4 mg/ml Poloxamer 188 or 30 mg/ml PEG 35000, at pH 9.4.

Typically the invention relates to a pharmaceutical formulation consisting of an aqueous solution of 3 mg/ml Arg$^{34}$, Lys$^{26}$(N-ε-(γ-Glu(N-α-hexadecanoyl)))-GLP-1(7-37), glycine, 36.9 mg/ml mannitol, 5 mg/ml phenol, and either 4 mg/ml Poloxamer 188 or 30 mg/ml PEG 35000, at pH 9.4.

Typically the invention relates to a pharmaceutical formulation consisting of an aqueous solution of 5 mg/ml Arg$^{34}$, Lys$^{26}$(N-ε-(γ-Glu(N-α-hexadecanoyl)))-GLP-1(7-37), glycine, 36.9 mg/ml mannitol, 5 mg/ml phenol, and either 4 mg/ml Poloxamer 188 or 30 mg/ml PEG 35000, at pH 9.4.

Typically the invention relates to a pharmaceutical formulation consisting of an aqueous solution of 1 mg/ml Arg$^{34}$, Lys$^{26}$(N-ε-(γ-Glu(N-α-hexadecanoyl)))-GLP-1(7-37), disodium hydrogen phosphate, 16.0 mg/ml glycerol, and 7 mg/ml phenol, at pH 8.4.

Typically the invention relates to a pharmaceutical formulation consisting of an aqueous solution of 2 mg/ml Arg$^{34}$, Lys$^{26}$(N-ε-(γ-Glu(N-α-hexadecanoyl)))-GLP-1(7-37), disodium hydrogen phosphate, 16.0 mg/ml glycerol, and 7 mg/ml phenol, at pH 8.4.

Typically the invention relates to a pharmaceutical formulation consisting of an aqueous solution of 3 mg/ml Arg$^{34}$, Lys$^{26}$(N-ε-(γ-Glu(N-α-hexadecanoyl)))-GLP-1(7-37), disodium hydrogen phosphate, 16.0 mg/ml glycerol, and 7 mg/ml phenol, at pH 8.4.

Typically the invention relates to a pharmaceutical formulation consisting of an aqueous solution of 5 mg/ml Arg$^{34}$, Lys$^{26}$(N-ε-(γ-Glu(N-α-hexadecanoyl)))-GLP-1(7-37), disodium hydrogen phosphate, 16.0 mg/ml glycerol, and 7 mg/ml phenol, at pH 8.4.

Typically the invention relates to a pharmaceutical formulation consisting of an aqueous solution of 7 mg/ml Arg$^{34}$, Lys$^{26}$(N-ε-(γ-Glu(N-α-hexadecanoyl)))-GLP-1(7-37), disodium hydrogen phosphate, 16.0 mg/ml glycerol, and 7 mg/ml phenol, at pH 8.4.

Typically the invention relates to a pharmaceutical formulation consisting of an aqueous solution of 1 mg/ml Arg$^{34}$, Lys$^{26}$(N-ε-(γ-Glu(N-α-hexadecanoyl)))-GLP-1(7-37), disodium hydrogen phosphate, 36.9 mg/ml mannitol, and 5 mg/ml phenol, at pH 8.4.

Typically the invention relates to a pharmaceutical formulation consisting of an aqueous solution of 2 mg/ml Arg$^{34}$, Lys$^{26}$(N-ε-(γ-Glu(N-α-hexadecanoyl)))-GLP-1(7-37), disodium hydrogen phosphate, 36.9 mg/ml mannitol, and 5 mg/ml phenol, at pH 8.4.

Typically the invention relates to a pharmaceutical formulation consisting of an aqueous solution of 3 mg/ml Arg$^{34}$, Lys$^{26}$(N-ε-(γ-Glu(N-α-hexadecanoyl)))-GLP-1(7-37), disodium hydrogen phosphate, 36.9 mg/ml mannitol, and 5 mg/ml phenol, at pH 8.4.

Typically the invention relates to a pharmaceutical formulation consisting of an aqueous solution of 5 mg/ml Arg$^{34}$, Lys$^{26}$(N-ε-(γ-Glu(N-α-hexadecanoyl)))-GLP-1(7-37), disodium hydrogen phosphate, 36.9 mg/ml mannitol, and 5 mg/ml phenol, at pH 8.4.

Typically the invention relates to a pharmaceutical formulation consisting of an aqueous solution of 7 mg/ml Arg$^{34}$, Lys$^{26}$(N-ε-(γ-Glu(N-α-hexadecanoyl)))-GLP-1(7-37), disodium hydrogen phosphate, 36.9 mg/ml mannitol, and 5 mg/ml phenol, at pH 8.4.

Typically the invention relates to a pharmaceutical formulation consisting of an aqueous solution of 1 mg/ml Arg$^{34}$, Lys$^{26}$(N-ε-(γ-Glu(N-α-hexadecanoyl)))-GLP-1(7-37), disodium hydrogen phosphate, 36.9 mg/ml mannitol, 5 mg/ml phenol, and 1.55 mg/ml L-His, at pH 8.4.

Typically the invention relates to a pharmaceutical formulation consisting of an aqueous solution of 2 mg/ml Arg$^{34}$, Lys$^{26}$(N-ε-(γ-Glu(N-α-hexadecanoyl)))-GLP-1(7-37), disodium hydrogen phosphate, 36.9 mg/ml mannitol, 5 mg/ml phenol, and 1.55 mg/ml L-His, at pH 8.4.

Typically the invention relates to a pharmaceutical formulation consisting of an aqueous solution of 3 mg/ml $Arg^{34}$, $Lys^{26}$(N-ε-(γ-Glu(N-α-hexadecanoyl)))-GLP-1(7-37), disodium hydrogen phosphate, 36.9 mg/ml mannitol, 5 mg/ml phenol, and 1.55 mg/ml L-His, at pH 8.4.

Typically the invention relates to a pharmaceutical formulation consisting of an aqueous solution of 5 mg/ml $Arg^{34}$, $Lys^{26}$(N-ε-(γ-Glu(N-α-hexadecanoyl)))-GLP-1(7-37), disodium hydrogen phosphate, 36.9 mg/ml mannitol, 5 mg/ml phenol, and 1.55 mg/ml L-His, at pH 8.4.

Typically the invention relates to a pharmaceutical formulation consisting of an aqueous solution of 7 mg/ml $Arg^{34}$, $Lys^{26}$(N-ε-(γ-Glu(N-α-hexadecanoyl)))-GLP-1(7-37), disodium hydrogen phosphate, 36.9 mg/ml mannitol, 5 mg/ml phenol, and 1.55 mg/ml L-His, at pH 8.4.

Any possible combination of two or more of the embodiments described herein is comprised within the scope of the present invention.

The parent peptide, GLP-1(7-37) or analogue thereof, can be produced by a method which comprises culturing a host cell containing a DNA sequence encoding the polypeptide and capable of expressing the polypeptide in a suitable nutrient medium under conditions permitting the expression of the peptide, after which the resulting peptide is recovered from the culture.

The medium used to culture the cells may be any conventional medium suitable for growing the host cells, such as minimal or complex media containing appropriate supplements. Suitable media are available from commercial suppliers or may be prepared according to published recipes (e.g. in catalogues of the American Type Culture Collection). The peptide produced by the cells may then be recovered from the culture medium by conventional procedures including separating the host cells from the medium by centrifugation or filtration, precipitating the proteinaceous components of the supernatant or filtrate by means of a salt, e.g. ammonium sulphate, purification by a variety of chromatographic procedures, e.g. ion exchange chromatography, gel filtration chromatography, affinity chromatography, or the like, dependent on the type of peptide in question.

The DNA sequence encoding the parent peptide may suitably be of genomic or cDNA origin, for instance obtained by preparing a genomic or cDNA library and screening for DNA sequences coding for all or part of the peptide by hybridisation using synthetic oligonucleotide probes in accordance with standard techniques (see, for example, Sambrook, J, Fritsch, E F and Maniatis, T, *Molecular Cloning: A Laboratory Manual*, Cold Spring Harbor Laboratory Press, New York, 1989). The DNA sequence encoding the peptide may also be prepared synthetically by established standard methods, e.g. the phosphoamidite method described by Beaucage and Caruthers, *Tetrahedron Letters* 22 (1981), 1859-1869, or the method described by Matthes et al., *EMBO Journal* 3 (1984), 801-805. The DNA sequence may also be prepared by polymerase chain reaction using specific primers, for instance as described in U.S. Pat. No. 4,683,202 or Saiki et al., *Science* 239 (1988), 487-491.

The DNA sequence may be inserted into any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The vector is preferably an expression vector in which the DNA sequence encoding the peptide is operably linked to additional segments required for transcription of the DNA, such as a promoter. The promoter may be any DNA sequence which shows transcriptional activity in the host cell of choice and may be derived from genes encoding proteins either homologous or heterologous to the host cell. Examples of suitable promoters for directing the transcription of the DNA encoding the peptide of the invention in a variety of host cells are well known in the art, cf. for instance Sambrook et al., supra.

The DNA sequence encoding the peptide may also, if necessary, be operably connected to a suitable terminator, polyadenylation signals, transcriptional enhancer sequences, and translational enhancer sequences. The recombinant vector of the invention may further comprise a DNA sequence enabling the vector to replicate in the host cell in question.

The vector may also comprise a selectable marker, e.g. a gene the product of which complements a defect in the host cell or one which confers resistance to a drug, e.g. ampicillin, kana-mycin, tetracyclin, chloramphenicol, neomycin, hygromycin or methotrexate.

To direct a parent peptide of the present invention into the secretory pathway of the host cells, a secretory signal sequence (also known as a leader sequence, prepro sequence or pre sequence) may be provided in the recombinant vector. The secretory signal sequence is joined to the DNA sequence encoding the peptide in the correct reading frame. Secretory signal sequences are commonly positioned 5' to the DNA sequence encoding the peptide. The secretory signal sequence may be that normally associated with the peptide or may be from a gene encoding another secreted protein.

The procedures used to ligate the DNA sequences coding for the present peptide, the promoter and optionally the terminator and/or secretory signal sequence, respectively, and to insert them into suitable vectors containing the information necessary for replication, are well known to persons skilled in the art (cf., for instance, Sambrook et al., supra).

The host cell into which the DNA sequence or the recombinant vector is introduced may be any cell which is capable of producing the present peptide and includes bacteria, yeast, fungi and higher eukaryotic cells. Examples of suitable host cells well known and used in the art are, without limitation, *E. coli, Saccharomyces cerevisiae*, or mammalian BHK or CHO cell lines.

Examples of Pharmaceutical Formulations

In the following "Compound 1" is intended to mean: $Arg^{34}$, $Lys^{26}(N^{\epsilon}\text{-}(\gamma\text{-}Glu(N^{\alpha}\text{-}hexadecanoyl)))$ GLP-1(7-37).

Physical stability of the formulations is evaluated by means of visual inspection and turbidity after storage of the formulation in top filled glass cartridges for various time periods. The cartridges are stored at 5° C.±3° C. and/or at elevated temperatures (e.g. 25° C. or 37° C.).

Visual inspection of the formulations is performed in a sharp focused light with a dark background. The turbidity of the formulation is characterized by a visual score ranking the degree of turbidity from 0 to 3 (a formulation showing no turbidity corresponds to a visual score 0, and a formulation showing visual turbidity in daylight corresponds to visual score 3). A formulation is classified physical unstable with respect to protein aggregation, when it shows visual turbidity in daylight.

The turbidity is also measured in Nephelometric Turbidity Units (NTU) with a nephelometer, which has been calibrated with a Formazin standard. A formulation with a turbidity>10 NTU is regarded as physical unstable.

Infrared measurements have shown that the turbididy is protein related. Hence, precipitate in a turbid Compound 1 sample has been isolated after centrifugation as a semisolid pellet. Fourier Transform Infrared measurements in the amide region on the pellet shows high absorption and increased amounts of β-sheet structure and a concomitant decrease in α-helix relative to compound 1 in solution, which is consistent with aggregated compound 1.

Example 1

Preservative, isotonic agent and buffer were dissolved and pH was adjusted to the specified pH. Hereafter the Compound 1 or GLP1(7-37) was dissolved under slow stirring. The pH was adjusted to the specified using Sodium Hydroxide and/or Hydrochloric Acid. Finally, the formulation was sterilised by filtration through a 0.22 μm sterile filter.

It is seen that a formulation with GLP1(7-37) is physically unstable after just 1 day as it has a visual score corresponding to 3 and a turbidity of 364 NTU, whereas a formulation with Compound 1 is physically stable for more than 12 weeks.

Example 2

Buffer was dissolved and pH was adjusted to the specified pH. Hereafter the Compound 1 was dissolved under slow stirring. The pH was adjusted to the specified using Sodium Hydroxide and/or Hydrochloric Acid. Finally, the formulation was sterilised by filtration through a 0.22 μm sterile filter. The physical stability is evaluated by visual inspection and Turbidity measurements in NTU as described in Example 1.

| Amount of compound 1 | PH | Buffer | Visual inspection at 5° C. (visual score) | Turbidity measurements at 5° C. (NTU) |
|---|---|---|---|---|
| 80 mg/ml | 7.4 | Disodium hydrogen phosphate | 1 (8 months) | 4.7 (10 months) |
| 80 mg/ml | 7.4 | Disodium hydrogen phosphate | 1 (22 months) | 4.9 (22 months) |

It is seen that the formulation is physically stable for more than 22 months.

Example 3

Preservative and buffer was dissolved and pH was adjusted to the specified pH. Hereafter the Compound 1 was dissolved under slow stirring. The pH was adjusted to the specified using Sodium Hydroxide and/or Hydrochloric Acid. Finally, the formulation was sterilised by filtration through a 0.22 μm sterile filter.

The physical stability is evaluated by visual inspection and Turbidity measurements in NTU as described in Example 1.

| Compound | Amount | pH | Buffer | Isotonic agent | Preservative | Visual inspection at 5° C. (visual score) | Turbidity measurements at 5° C. (NTU) |
|---|---|---|---|---|---|---|---|
| $Arg^{34}$, $Lys^{26}(N^{\epsilon}\text{-}(\gamma\text{-}Glu(N^{\alpha}\text{-}hexadecanoyl)))$ GLP-1 (7-37). | 3 mg/ml | 7.9 | Disodium hydrogen phosphate | Mannitol 36.9 mg/ml | Phenol 5 mg/ml | 1.5 (12 weeks) | 0.9 (6 weeks) |
| GLP1(7-37) | 3 mg/ml | 7.9 | Disodium hydrogen phosphate | Mannitol 36.9 mg/ml | Phenol 5 mg/ml | 3 (1 day) | 364 (1 day) |

| Amount of compound 1 | PH | Buffer | Preservative | Visual inspection at 5° C. (visual score) | Turbidity measurements at 5° C. (NTU) |
|---|---|---|---|---|---|
| 80 mg/ml | 7.4 | Disodium hydrogen phosphate | Phenol 10 mg/ml | 1 (8 months) | 4.3 (10 months) |
| 80 mg/ml | 7.4 | Disodium hydrogen phosphate | Phenol 10 mg/ml | 1 (22 months) | 5.3 (22 months) |

It is seen that the formulation is physically stable for more than 10 months and even for more than 22 months.

Example 4

Preservative, isotonic agent and buffer were dissolved and pH was adjusted to the specified pH. Hereafter the Compound 1 was dissolved under slow stirring. The pH was adjusted to the specified using Sodium Hydroxide and/or Hydrochloric Acid. Finally, the formulation was sterilised by filtration through a 0.22 µm sterile filter.

The physical stability is evaluated by visual inspection and Turbidity measurements in NTU as described in Example 1.

It is seen that some of the formulations has already been measured to be stable for more than 14 months and some more than 22 months.

Example 5

Preservative, isotonic agent, buffer, and further additive(s) selected from chelating agent, stabiliser and surfactant were dissolved and pH was adjusted to the specified pH. Hereafter the Compound 1 was dissolved under slow stirring. The pH was adjusted to the specified using Sodium Hydroxide and/or Hydrochloric Acid. Finally, the formulation was sterilised by filtration through a 0.22 µm sterile filter.

The physical stability is evaluated by visual inspection and Turbidity measurements in NTU as described in Example 1.

| Amount of Compound 1 | PH | Buffer | Isotonic agent | Preservative | Visual inspection at 5° C. (visual score) | Turbidity measurements at 5° C. (NTU) |
|---|---|---|---|---|---|---|
| 0.3 mg/ml | 7.4 | Sodium dihydrogen phosphate/ disodium hydrogen phosphate | Mannitol 36.9 mg/ml | Phenol 5 mg/ml | 0 (24 months) | 0.6 (24 months) |
| 3 mg/ml | 7.9 | glycylglycine | Glycerol 16.0 mg/ml | Phenol 5 mg/ml | 0.5 (12 weeks) | 2.1 (6 weeks) |
| 3 mg/ml | 7.9 | glycylglycine | Glycerol 16.0 mg/ml | Phenol 5 mg/ml | 1 (15 months) | 0.7 (15 months) |
| 1 mg/ml | 7.0 | Sodium dihydrogen phosphate/ disodium hydrogen phosphate | Mannitol 17.0 mg/ml | Benzylalcohol 18 mg/ml | 0.5 (9 months) | 1.7 (11 months) |
| 1 mg/ml | 7.0 | Sodium dihydrogen phosphate/ disodium hydrogen phosphate | Mannitol 17.0 mg/ml | Benzylalcohol 18 mg/ml | 0.5 (22 months) | 1.7 (22 months) |
| 1 mg/ml | 7.0 | Sodium dihydrogen phosphate/ disodium hydrogen phosphate | Mannitol 38.5 mg/ml | m-cresol (3 mg/ml) and phenol (1.5 mg/ml) | 0 (9 months) | 1.5 (11 months) |
| 1 mg/ml | 7.0 | Sodium dihydrogen phosphate/ disodium hydrogen phosphate | Mannitol 38.5 mg/ml | m-cresol (3 mg/ml) and phenol (1.5 mg/ml) | 0.5 (22 months) | 1.9 (22 months) |
| 5 mg/ml | 7.8 | Sodium dihydrogen phosphate/ disodium hydrogen phosphate | Mannitol 17.0 mg/ml | Benzylalcohol 18 mg/ml | 0.5 (9 months) | 1.8 (11 months) |
| 5 mg/ml | 7.8 | Sodium dihydrogen phosphate/ disodium hydrogen phosphate | Mannitol 17.0 mg/ml | Benzylalcohol 18 mg/ml | 1 (22 months) | 1.5 (22 months) |
| 3 mg/ml | 9.4 | glycine | Mannitol 36.9 mg/ml | Phenol 5 mg/ml | 0.5 (2½ months) | 0.7 (2 months) |
| 3 mg/ml | 9.4 | glycine | Mannitol 36.9 mg/ml | Phenol 5 mg/ml | 1 (14 months) | 0.7 (14 months) |

| Amount of compound 1 | PH | Buffer | Isotonic agent | Preservative | Chelating agent/stabiliser/surfactant | Visual inspection at 5° C. (visual score) | Turbidity measurements at 5° C. (NTU) |
|---|---|---|---|---|---|---|---|
| 3 mg/ml | 9.4 | Glycine | Mannitol 36.9 mg/ml | Phenol 5 mg/ml | EDTA (1 mg/ml)/ L-Histidin (1.55 mg/ml) | 0.5 (2½ months) | 1.2 (2 months) |
| 3 mg/ml | 9.4 | Glycine | Mannitol 36.9 mg/ml | Phenol 5 mg/ml | EDTA (1 mg/ml)/ L-Histidin (1.55 mg/ml) | 0.5 (14 months) | 0.9 (14 months) |
| 3 mg/ml | 9.4 | glycine | Mannitol 36.9 mg/ml | Phenol 5 mg/ml | Poloxamer 188 (4 mg/ml)/ PEG 35000 (30 mg/ml) | 1 (2½ months) | 1.3 (2 months) |
| 3 mg/ml | 9.4 | glycine | Mannitol 36.9 mg/ml | Phenol 5 mg/ml | Poloxamer 188 (4 mg/ml)/ PEG 35000 (30 mg/ml) | 1 (14 months) | 0.8 (14 months) |
| 80 mg/ml | 7.4 | Disodium hydrogen phosphate | none | none | LPCM 19 mg/ml | 0 (8 months) | 7.3 (10 months) |
| 80 mg/ml | 7.4 | Disodium hydrogen phosphate | none | none | LPCM 19 mg/ml | 1 (22 months) | 8.1 (22 months) |

It is seen that some of the formulations has already been measured to be stable for more than 14 months and some more than 22 months.

Example 6

Preservative, isotonic agent and buffer were dissolved and pH adjusted to the specified pH. Hereafter the Compound was dissolved under slow stirring. The pH was adjusted to the specified using Sodium Hydroxide and/or Hydrochloric Acid. Finally, the formulation was sterilised by filtration through a 0.22 μm sterile filter. The physical stability was followed at 5, 25 and 37° C.

The physical stability is evaluated by visual inspection and Turbidity measurements in NTU as described in Example 1.

| Amount of Compound 1 | PH | Buffer | Isotonic agent | Preservative | Temp. | Visual inspection (visual score) | Turbidity measurements (NTU) |
|---|---|---|---|---|---|---|---|
| 3 mg/ml | 8.4 | Disodium hydrogen phosphate | Glycerol 16.0 mg/ml | Phenol 7 mg/ml | 5° C. | 0.5 (12 weeks) | 1.0 (6 weeks) |
| 3 mg/ml | 8.4 | Disodium hydrogen phosphate | Glycerol 16.0 mg/ml | Phenol 7 mg/ml | 5° C. | 1 (15 months) | 0.6 (15 months) |
| 3 mg/ml | 8.4 | Disodium hydrogen phosphate | Glycerol 16.0 mg/m | Phenol 7 mg/ml | 25° C. | 0.5 (12 weeks) | 1.00 (8 weeks) |
| 3 mg/ml | 8.4 | Disodium hydrogen phosphate | Glycerol 16.0 mg/m | Phenol 7 mg/ml | 37° C. | 1 (12 weeks) | 1.1 (8 weeks) |

It is seen that the formulation is physically stable after storage at 5° C. for more than 15 months and after storage at 25 and 37° C. it is physically stable for more than 12 weeks.

Example 7

The chemical stability of modified GLP-1 can be significantly improved by the use of certain amino acids (charged-basic) and imidazole as stabilizers.

| Composition | pH | Temperature | Purity, Compound 1 (%) T = 12 weeks | Dimer formation, Compound 1 (%) T = 12 weeks |
|---|---|---|---|---|
| 3 mg/ml Compound 1<br>1.42 mg/ml disodium hydrogenphosphate, dihydrate<br>5 mg/ml phenol<br>36.9 mg/ml mannitol | 7.4 | 37° C. | 78.4 | 5.43 |
| 3 mg/ml Compound 1<br>1.42 mg/ml disodium hydrogenphosphate, dihydrate<br>5 mg/ml phenol<br>36.9 mg/ml mannitol<br>1.55 mg/ml L-histidine | 7.4 | 37° C. | 85.9 | 3.28 |
| 3 mg/ml Compound 1<br>1.42 mg/ml disodium hydrogenphosphate, dihydrate<br>5 mg/ml phenol | 7.4 | 37° C. | 86.2 | 1.88 |
| 36.9 mg/ml mannitol<br>7.75 mg/ml L-histidine<br>3 mg/ml Compound 1<br>1.42 mg/ml disodium hydrogenphosphate, dihydrate<br>5 mg/ml phenol | 7.4 | 37° C. | 85.3 | 3.70 |
| 36.9 mg/ml mannitol<br>1.74 mg/ml L-arginine<br>3 mg/ml Compound 1<br>1.42 mg/ml disodium hydrogenphosphate, dihydrate<br>5 mg/ml phenol | 7.4 | 37° C. | 74.3 | 3.42 |
| 36.9 mg/ml mannitol<br>0.68 mg/ml imidazole<br>2 mg/ml Compound 1<br>1.42 mg/ml disodium hydrogenphosphate, dihydrate<br>5.5 mg/ml phenol<br>16 mg/ml glycerol | 7.7 | 37° C. | 88.5 | 7.74 |
| 2 mg/ml Compound 1<br>1.42 mg/ml disodium hydrogenphosphate, dihydrate<br>5.5 mg/ml phenol<br>16 mg/ml glycerol | 8.0 | 37° C. | 88.2 | 7.62 |
| 2 mg/ml Compound 1<br>1.42 mg/ml disodium hydrogenphosphate, dihydrate<br>5.5 mg/ml phenol<br>16 mg/ml glycerol<br>1.55 mg/ml histidine | 7.7 | 37° C. | 90.4 | 4.71 |
| 2 mg/ml Compound 1<br>1.42 mg/ml disodium hydrogenphosphate, dihydrate<br>5.5 mg/ml phenol<br>16 mg/ml glycerol<br>1.55 mg/ml histidine | 8.0 | 37° C. | 90.6 | 4.67 |

From the above table it appears that the purity of Compound 1, analyzed by RP-HPLC, is significantly improved in preparations comprising histidine or arginine as stabilizers. Furthermore the formation of Compound 1 dimers, analyzed by SE-HPLC, is clearly reduced in preparations with imidazole, histidine and arginine.

The invention claimed is:

1. A pharmaceutical formulation comprising:
a GLP-1 compound, wherein said GLP-1 compound is: Arg$^{34}$, Lys$^{26}$(N-ε-(γ-Glu(N-α-hexadecanoyl)))-GLP-1 (7-37),
and wherein said GLP-1 compound binds to a GLP-1 receptor with an affinity constant ($K_D$) below about 1 μM or a potency $EC_{50}$ below about 1 μM, and wherein said GLP-1 compound is present in a concentration from 0.1 mg/ml to 100 mg/ml;
an isotonic agent;
a buffer; and
a preservative;
wherein said pharmaceutical formulation has a pH from 7.5 to 9.4.

2. The formulation according to claim 1, further comprising water.

3. The formulation according to claim 1, wherein the concentration of said GLP-1 compound is from 0.1 mg/ml to 10 mg/ml.

4. The formulation according to claim 1, wherein the concentration of said GLP-1 compound is 1-5 mg/ml.

5. The formulation according to claim 1, wherein said preservative is present in a concentration from 0.1 mg/ml to 20 mg/ml.

6. The formulation according to claim 1, wherein said isotonic agent is present in a concentration from 1 mg/ml to 50 mg/ml.

7. The formulation according to claim 1, further comprising a chelating agent.

8. The formulation according to claim 7, wherein said chelating agent is present in a concentration from 0.1 mg/ml to 5 mg/ml.

9. The formulation according to claim 1, further comprising a stabiliser.

10. The formulation according to claim 9, wherein said stabiliser is selected from the group consisting of L-histidine, imidazole and arginine.

11. The formulation according to claim 9, wherein said stabiliser is a high molecular weight polymer and/or a low molecular weight compound and is present in a concentration from 0.1 mg/ml to 50 mg/ml.

12. The formulation according to claim 1, further comprising a surfactant.

13. A method of preparing a physically stable pharmaceutical formulation of a GLP-1 compound wherein said GLP-1 compound is Arg$^{34}$, Lys$^{26}$(N-ε-(γ-Glu(N-α-hexadecanoyl)))-GLP-1(7-37), and wherein said GLP-1 compound binds to a GLP-1 receptor with an affinity constant ($K_D$) below about 1 μM or a potency $EC_{50}$ below about 1 μM, said method comprising preparing a formulation containing the GLP-1 compound, an isotonic agent, a preservative, and a buffer, wherein said GLP-1 compound is present in a concentration from 0.1 mg/ml to 100 mg/ml, and
wherein said formulation has a pH from 7.5 to 9.4.

14. A pharmaceutical formulation comprising:
a GLP-1 compound, wherein said GLP-1 compound is Arg$^{34}$, Lys$^{26}$(N-ε-(γ-Glu(N-α-hexadecanoyl)))-GLP-1 (7-37), and wherein said GLP-1 compound binds to a GLP-1 receptor with an affinity constant ($K_D$) below about 1 μM or a potency $EC_{50}$ below about 1 μM;
an isotonic agent;
a buffer; and
a preservative;
wherein said pharmaceutical formulation has a pH from 7.5 to 9.4.

* * * * *

SEQUENCE LISTING

<160> NUMBER OF SEQ ID NOS: 1

<210> SEQ ID NO 1
<211> LENGTH: 31
<212> TYPE: PRT
<213> ORGANISM: Homo sapiens

```
<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30
```